United States Patent [19]

Ecker et al.

[11] Patent Number: 5,702,427
[45] Date of Patent: Dec. 30, 1997

[54] VERIFICATION OF CAPTURE USING PRESSURE WAVES TRANSMITTED THROUGH A PACING LEAD

[75] Inventors: Robert M. Ecker, Anoka; Lawrence C. McClure, Maple Grove; John D. Wahlstrand, Shoreview, all of Minn.

[73] Assignee: Medtronic, Inc., Minneapolis, Minn.

[21] Appl. No.: 623,443

[22] Filed: Mar. 28, 1996

[51] Int. Cl.$^6$ .............................. A61N 1/375; A61N 1/365
[52] U.S. Cl. ............................... 607/28; 607/36; 607/37
[58] Field of Search .............................. 607/18–20, 28, 607/36, 37

[56] References Cited

U.S. PATENT DOCUMENTS

| | | | |
|---|---|---|---|
| 4,023,562 | 5/1977 | Hynecek | 128/748 |
| 4,114,628 | 9/1978 | Rizk | 607/4 |
| 4,305,396 | 12/1981 | Wittkampf | 607/25 |
| 4,374,382 | 2/1983 | Markowitz | 607/27 |
| 4,407,296 | 10/1983 | Anderson | 128/675 |
| 4,428,378 | 1/1984 | Anderson | 607/19 |
| 4,432,372 | 2/1984 | Monroe | 128/675 |
| 4,485,813 | 12/1984 | Anderson | 128/675 |
| 4,556,063 | 12/1985 | Thompson | 607/32 |
| 4,729,376 | 3/1988 | Decote | 607/28 |
| 4,763,646 | 8/1988 | Lekholm | 607/28 |
| 4,795,366 | 1/1989 | Tetreault | 439/476.1 |
| 4,858,610 | 8/1989 | Callaghan | 607/28 |
| 4,858,615 | 8/1989 | Meinema | 128/668 |
| 4,878,497 | 11/1989 | Callaghan | 607/28 |
| 4,967,755 | 11/1990 | Pohndorf | 128/675 |
| 5,069,680 | 12/1991 | Grandjean | 623/3 |
| 5,080,096 | 1/1992 | Hooper et al. | 607/19 |
| 5,165,404 | 11/1992 | Andersson | 607/13 |
| 5,165,405 | 11/1992 | Eckwall | 607/13 |
| 5,172,690 | 12/1992 | Nappholz | 607/13 |
| 5,222,493 | 6/1993 | Sholder | 607/27 |
| 5,226,413 | 7/1993 | Bennett et al. | 607/18 |
| 5,285,780 | 2/1994 | Tsuji | 607/13 |
| 5,312,441 | 5/1994 | Mader | 607/5 |
| 5,320,643 | 6/1994 | Roline | 607/28 |
| 5,324,310 | 6/1994 | Greeninger | 607/28 |
| 5,324,326 | 6/1994 | Lubin | 607/122 |
| 5,331,966 | 7/1994 | Bennett | 607/28 |
| 5,480,414 | 1/1996 | Stroebel et al. | 607/28 |
| 5,502,388 | 3/1996 | Melzer | 324/438 |
| 5,556,421 | 9/1996 | Prutchi et al. | 607/36 |

FOREIGN PATENT DOCUMENTS 9413200  6/1994  WIPO ................. A61B 5/03

OTHER PUBLICATIONS

37150 "Use of Heart Valve Sounds as Input to Cardiac Assist Devices", *Research Disclosure*, Mar., 1995, p. 184 (disclosed anonymously).

Ko et al., "A Design of Capacitive Pressure Transducer", Electrical Engineering and Applied Physics Dept. and Electronics Design Center, Case Western University, Cleveland OH 44106 p. 32.

*Primary Examiner*—William E. Kamm
*Assistant Examiner*—Carl H. Layno
*Attorney, Agent, or Firm*—Harold R. Patton; Michael B. Atlass

[57] ABSTRACT

A capture verification system for a cardiac pacemaker comprising an implantable pulse generator (IPG) and one or more pacing leads having a proximal end coupled to the IPG and a distal end in contact with a patient's heart. The capture verification system employs a pressure wave sensor mounted in the IPG in relation to the proximal end of the pacing lead for sensing pressure waves transmitted from the distal end of the pacing lead to the proximal end thereof. The pressure waves include characteristic sounds of heart contraction and/or distal end lead motion caused by the contraction motion of the patient's heart that are transmitted along the lead body to the active sensor. A further isolated, reference sensor is also incorporated into the IPG in a similar fashion. Signal processors are coupled to the pressure wave and reference sensors for nulling out common mode noise.

18 Claims, 9 Drawing Sheets

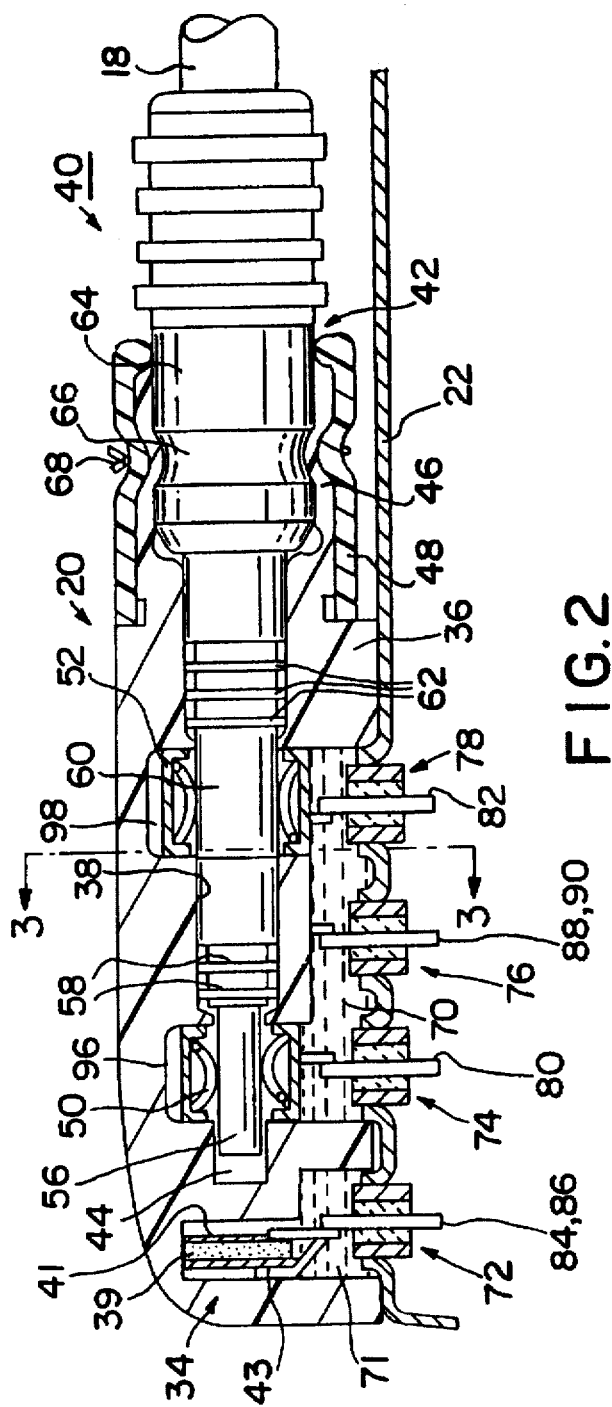
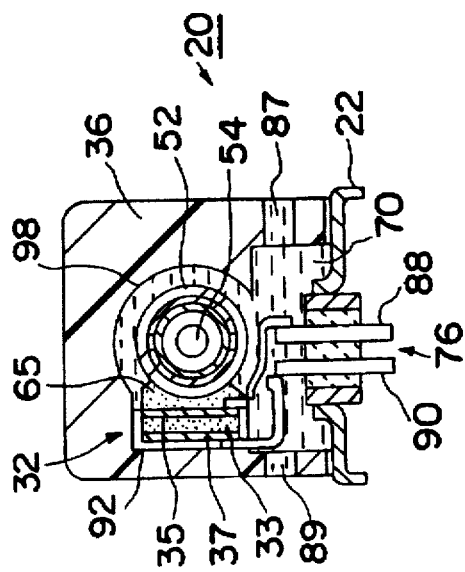
FIG. 2
FIG. 3

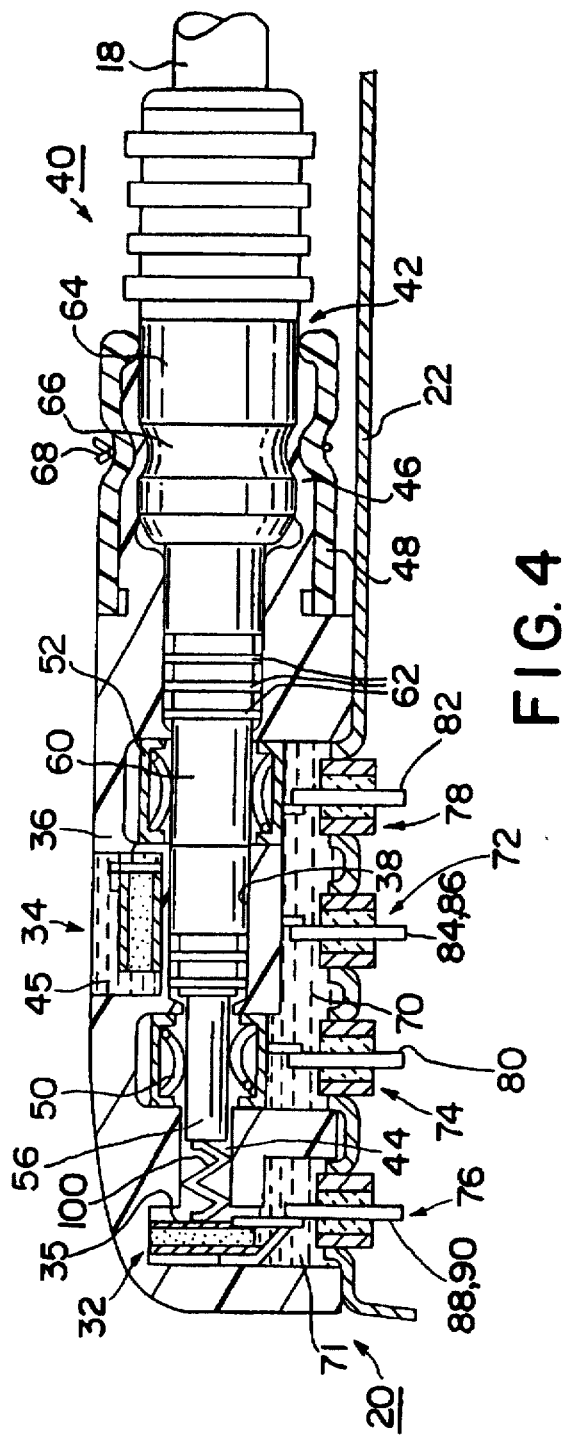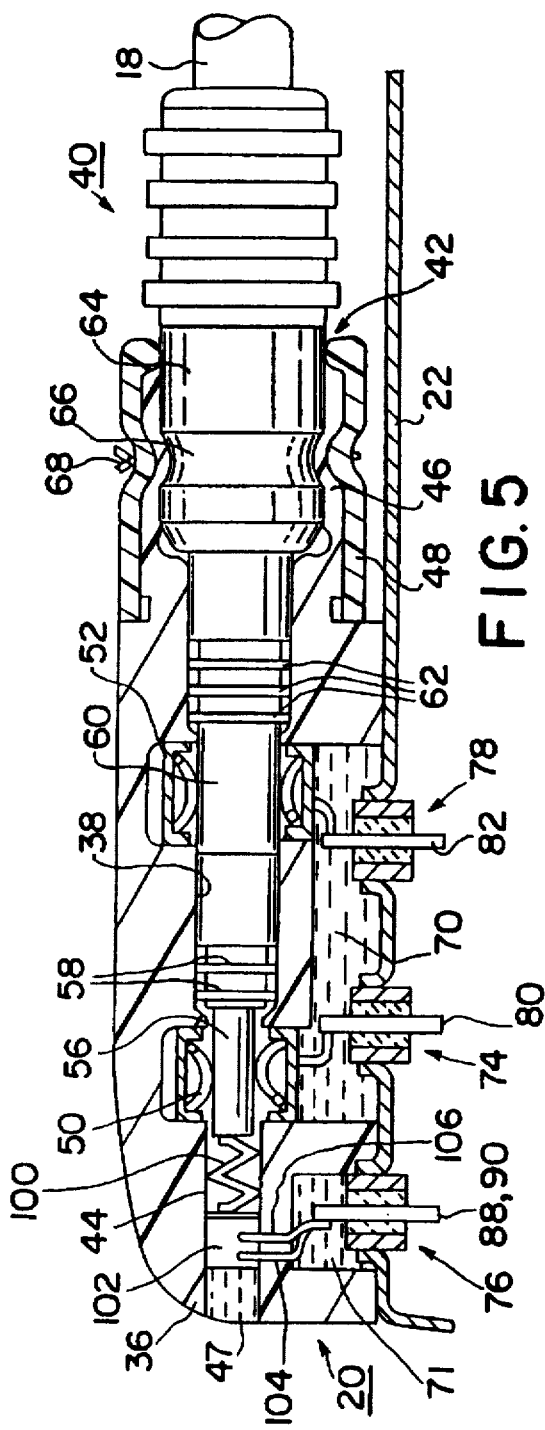

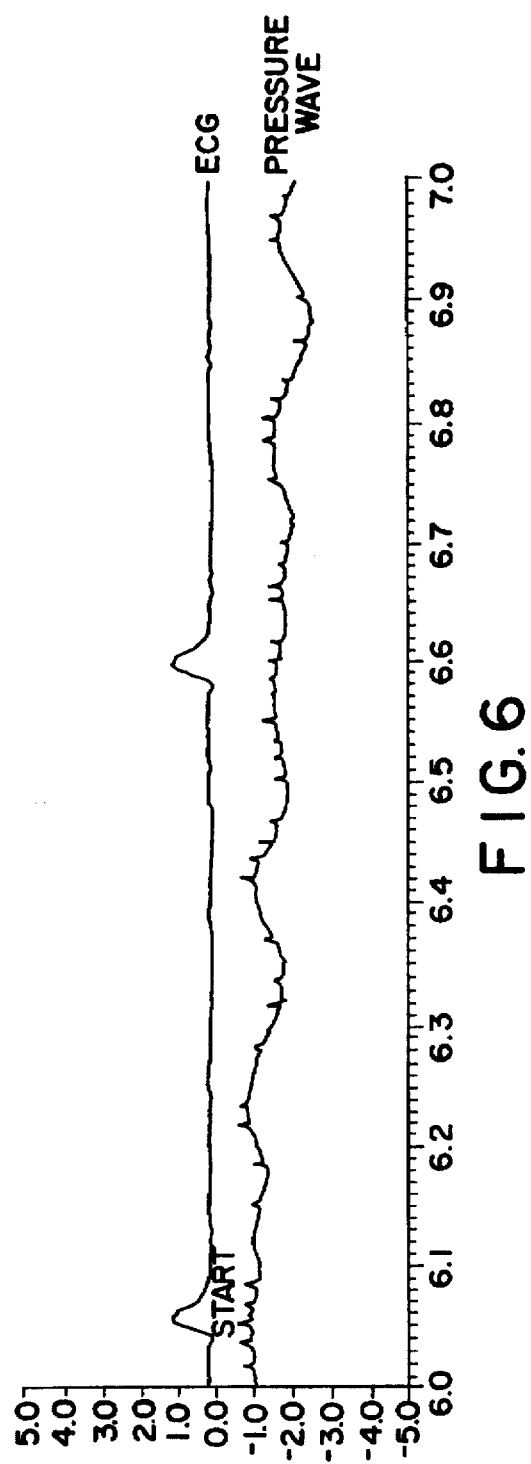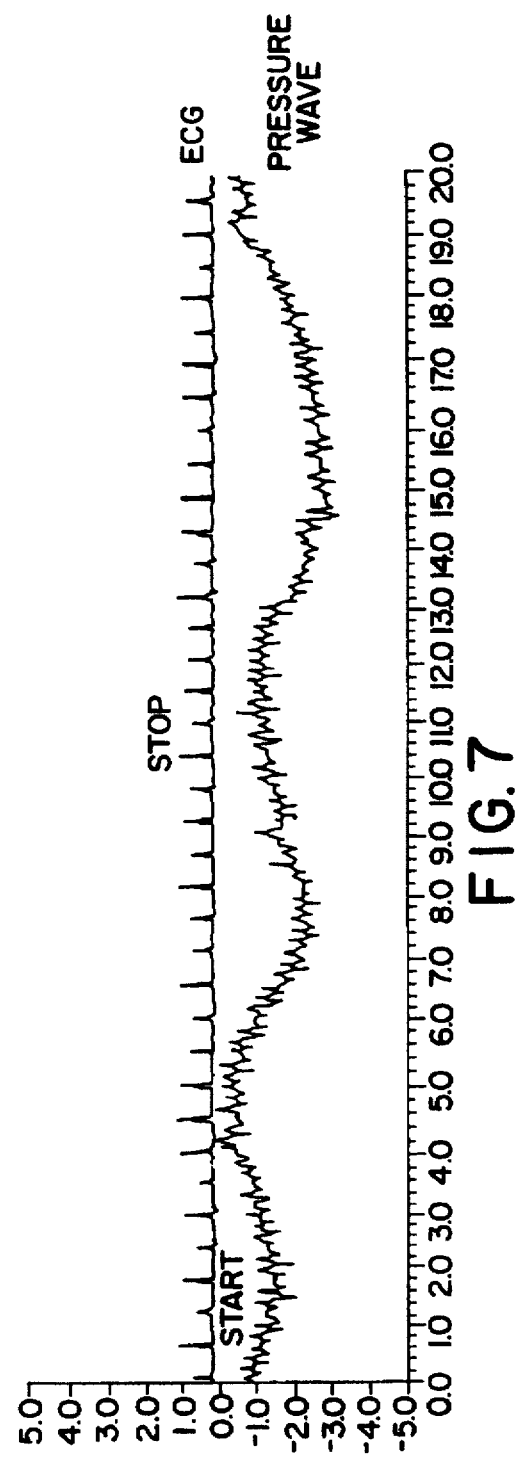

VERIFICATION OF CAPTURE USING PRESSURE WAVES TRANSMITTED THROUGH A PACING LEAD

CROSS-REFERENCE TO RELATED APPLICATION

Reference is hereby made to commonly assigned U.S. patent application Ser. Nos. 08/623,029 filed on even date herewith and entitled DETECTION OF PRESSURE WAVES TRANSMITTED THROUGH CATHETER/LEAD BODY and Ser. No. 08/623,477 filed on even date herewith and entitled RATE RESPONSIVE PACEMAKER.

FIELD OF THE INVENTION

The present invention generally relates to implantable pacemakers and more particularly to a method and apparatus for testing and detecting capture of the heart in both chambers of the heart, deriving and storing stimulation signal threshold data, and adjusting stimulation signal energy for energy efficiency.

BACKGROUND OF THE INVENTION

As described in commonly assigned U.S. Pat. No. 5,320,643, incorporated herein by reference, a cardiac pacemaker implantable pulse generator (IPG) is an electrical device used to supplant some or all of an abnormal heart's natural pacing function by delivering appropriately timed electrical stimulation signals designed to cause the myocardium of the heart to contract or "beat", i.e. to "capture" the heart. Stimulation pulses provided by implanted pacemakers usually have well-defined amplitude and pulse width characteristics which can be adjusted by remote programming and telemetry equipment to meet physiologic and device power conservation needs of the particular patient.

The strength (amplitude) and duration (pulse width) of the pacing pulses must be of such an energy magnitude above the stimulation threshold that capture is maintained to prevent serious complications and even death. Yet, it is desirable for these energy magnitudes not to be higher than the stimulation threshold than is needed for a reasonable "safety margin" in order to prolong battery life. The patient's stimulation thresholds in the atrium and ventricle often fluctuate in the short term, and gradually change in the long term. It has been clinically observed that the lowest stimulation threshold is observed immediately after implantation of the pacemaker (the acute threshold). Inflammation in the cardiac tissue around the tip of the pacing lead electrode drives the stimulation threshold up sharply during the first two to six weeks after implant to its highest level (the peak threshold), and greater pacing pulse energy is required to effect capture during this period. Some of the inflammation reduces over the long-term, to lower the threshold below the peak level—the chronic threshold. However, the chronic threshold does not reduce to the acute level, since some permanent fibrous tissue, requiring greater energy than non-fibrous tissue for signal propagation, remains around the electrode tip. In the short-term, thresholds may decrease with exercise, for example, and may increase with various activities, including sleep. Consequently, the safety margin is typically set by the physician on implantation of the pacemaker to account for projected maximal stimulation thresholds.

As described in commonly assigned U.S. Pat. No. 5,324,310, incorporated herein by reference, the post-operative determination of the stimulation thresholds by the physician typically requires the patient to be connected to surface ECG equipment while a threshold routine is conducted using the pacemaker programmer. The pacemaker programmer remotely effects the successive temporary reprogramming of the pulse width and/or amplitude to ascertain the points at which capture is lost, and a strength-duration curve may be plotted from the resulting threshold data. In this process, pacing pulses are delivered to either heart chamber at a test pacing rate above the patient's own underlying rate, and the pace pulse energy is decreased from pulse to pulse in a preset pattern. The pacing pulses are observed on a display or paper tracing as spikes, and capture or loss of capture (LOC) is observed by the presence or absence of the evoked cardiac response waveshape (a P-wave or an R-wave) that follows each spike. At LOC, the pacing pulse energy may be immediately restored so that the patient does not experience syncope. The resulting threshold data may be used to permanently reprogram the pulse energy. Naturally, such periodic patient studies are time consuming and expensive to conduct. Moreover, they do not provide an indication of stimulation threshold fluctuation over the course of a patient's day and levels of activity. The life of the IPG is shortened as the battery is depleted at a rate higher than necessary to meet the patient's needs.

As a result of these considerations, a great deal of effort has been expended over many years to develop IPGs having the capability of automatically testing the stimulation threshold, i.e. providing an "auto-capture" detection function, and resetting the pacing pulse energy to exceed the threshold by the safety margin without the need for clinical or patient intervention. A wide variety of approaches have been taken as reflected by the extensive listing of earlier patents described in the commonly assigned '310 and '643 patents and in further U.S. Pat. Nos. 5,165,404, 5,165,405, 5,172,690, 5,222,493, 5,285,780, and 5,331,966.

In such IPGs, the capture detection approaches have taken a variety of forms typically in the attempt to overcome the difficulty in detecting the evoked cardiac response wave shape from the pacing electrodes employed to deliver the pacing pulse. The high stimulation energy pacing pulse and the ensuing after-potentials and electrode-tissue polarization artifacts mask the evoked response, and also saturate the sense amplifiers coupled to the electrodes, until they dissipate. By the time that the sense amplifier is no longer blinded, the evoked response, if any, has typically passed the electrodes. Many of the approaches that have been taken include blanking intervals for the sense amplifiers combined with efforts to suppress or attenuate or compensate electronically for the composite post-delivery signal levels at the sense amplifier input during the blanking intervals to shorten the saturation period (and the blanking interval) as much as possible.

Alternatively, the use of separate "far field" EGM amplifiers and electrode systems from those "near field" electrode systems used in delivering the pacing pulse have been proposed in a variety of configurations, as exemplified by the above referenced '310 patent. Additional far-field electrodes and sense amplifiers are proposed in the above-referenced '966 and '493 patents.

In a further approach, a system disclosed in U.S. Pat. No. 4,114,628 suggests the use of a mechanical heart motion sensor in contact with the heart to detect capture or LOC. The disclosed sensor is a moving core, coiled wire inductor transducer mounted within an endocardial or epicardial lead coupled to the IPG.

The detection of heart sounds rather than the R-wave peak or a pressure sensor signal has also been suggested anonymously in RESEARCH DISCLOSURE No. 37150, entitled "Use of Heart Valve Sounds as Input to Cardiac Assist Devices" (March, 1995) for use in controlling operations of pulsatile cardiac assist devices. The listed cardiac assist devices include intra-atrial blood pumps (IABPs), cardiomyoplasty/cardiac assist devices (of the type described in commonly assigned U.S. Pat. No. 5,069,680, for example), aortomyoplasty and ventricular assist devices (VADs). The heart sounds are picked up by a microphone, amplified, bandpass filtered and compared to a "signature" sound pattern to derive a control signal timed to the second or "dub" heart sound, which is related to the dicrotic notch of the aortic pressure wave. No specific structure for accomplishing this is disclosed. In U.S. Pat. No. 4,763,646, a heart sound detector is proposed to be mounted in one or more pacing leads arranged in or about the heart or to be mounted in the IPG case for acoustically sensing heart sounds transmitted through a fluid filled lumen of a pacing lead. The use of a pressure sensor, microphone or accelerometer is proposed for the heart sound detector.

The system disclosed in the '643 patent employs a pressure sensor mounted at the end of a lead inserted transvenously to a position inside the heart chamber and an algorithm employing the pressure signal to determine the pacing threshold at which LOC occurs.

In this context, and in other IPG contexts, many different designs and operating systems have been proposed and placed into temporary or chronic use with patients for detecting heart contractions and/or measuring blood flow and systolic and diastolic pressure. Indwelling pressure sensors for temporary use of a few days or weeks are available, and many designs of chronically or permanently implantable pressure sensors have been placed in clinical use.

Piezoelectric crystal or piezoresistive pressure transducers mounted at or near the distal tips of pacing leads, for pacing applications, or catheters for monitoring applications, are described in U.S. Pat. Nos. 4,407,296, 4,432,372, 4,485,813, 4,858,615, 4,967,755, and 5,324,326, and PCT Publication No. WO 94/13200, for example. The desirable characteristics and applications for patient use of such lead or catheter bearing, indwelling pressure sensors are described in these and other patents and the literature in the field. Generally, the piezoelectric or piezoresistive transducers have to be sealed hermetically from blood. Certain of these patents, e.g. the '296 patent, disclose sealing the piezoresistive bridge elements within an oil filled chamber.

U.S. Pat. No. 4,023,562 describes a piezoresistive bridge of four, orthogonally disposed, semiconductor strain gauges formed interiorly on a single crystal silicon diaphragm area of a silicon base. A protective silicon cover is bonded to the base around the periphery of the diaphragm area to form a sealed, evacuated chamber. Deflection of the diaphragm due to ambient pressure changes is detected by the changes in resistance of the strain gauges.

Because the change in resistance is so small, a high current is required to detect the voltage change due to the resistance change. The high current requirements render the piezoresistive bridge unsuitable for long term use with an implanted power source. High gain amplifiers that are subject to drift over time are also required to amplify the resistance-related voltage change.

Other semiconductor sensors employ CMOS IC technology in the fabrication of pressure responsive silicon diaphragm bearing capacitive plates that are spaced from stationary plates. The change in capacitance due to pressure waves acting on the diaphragm is measured, typically through a bridge circuit, as disclosed, for example, in the article "A Design of Capacitive Pressure Transducer" by Ko et al., in *IEEE Proc. Symp. Biosensors*, 1984, p. 32. Again, fabrication for long term implantation and stability is complicated.

The function and accuracy of the these approaches for determining LOC have been adversely affected by one or more of factors including, but not limited to: myopotentials (electrical signals which are the product of muscle movement) and stray electromagnetic interference (EMI) in the case of EGMs; problems with the sensor sensitivity (either too sensitive or not sensitive enough) in case of other sensors; and, in the case of pressure sensors, variations in the pressure signal amplitudes as a result of changes in thoracic pressure (for example, due to respiration, coughing or sneezing) while the LOC algorithm is in effect. In addition, the indwelling pressure sensor approach requires the implantation of the sensor into the heart chamber where it may become fibrosed and lose its ability to respond to mechanical heart motion or blood pressure changes associated with the contraction of the heart chamber.

In virtually all of the approaches, it is necessary to rely on additional components, lead conductors and/or circuitry, e.g. the additional pressure sensing lead of the '643 patent or the heart motion detector of the '628 patent, which consume more energy, increase the bulk and cost of the system, increase the cost of the implantation, and raise reliability issues. This is true particularly in dual chamber pacemakers and in pacemaker-cardioverter-defibrillators.

Finally, the difficulty of detecting the evoked P-wave is further complicated by its relatively low amplitude. It is not feasible to detect the evoked P-wave by near-field or far-field EGM processes, especially in the atrium where the signal is smallest.

Despite the considerable effort that has been expended in designing such pressure sensors, very few of the capture detection approaches suggested in the prior art have been attempted in an implantable pacemaker system and fewer yet have been proven clinically useful and commercially successful.

A need exists therefore for a body implantable, durable, long lived, simple and low power sensor for accurately detecting both evoked P-waves and R-waves for use in determining the pacing energy threshold and automatically adjusting the delivered pacing pulse energy.

SUMMARY OF THE INVENTION

Accordingly, it is an object of the present invention to provide a practical and durable system for sensing the evoked response to a pacing pulse for determining the capture/LOC stimulation threshold in one or both chambers of the heart.

It is a further object of the present invention to provide a cardiac pacemaker having a capture detection feature without any significant additional special leads or electrodes, indwelling sensors or sophisticated processing of the evoked response signals.

These and other objects of the invention are realized in a system implemented in a cardiac pacemaker for verifying capture of the heart following delivery of a pacing pulse comprising:

a pacing lead comprising an elongated lead body extending between a proximal connector end and a distal end adapted to be placed in association with the heart such that heart motion effects motion of the lead distal end and the transmission of a pressure wave through the lead body, a pace/sense electrode at the distal end of the lead body, and a pace/sense lead conductor extending between the proximal connector end and the pace/sense electrode for conducting pacing pulses from the proximal connector end to the pace/sense electrode and for conducting electrogram heart signals from the pace/sense electrode to the proximal connector end; and a cardiac pacemaker pulse generator comprising a connector assembly for attachment with the proximal connector end, the connector assembly having a transducer mounted therein in relation to the proximal connector end for detecting the pressure wave and providing a heart signal representative thereof, a pulse generator for generating and delivering a pacing pulse through the connector assembly and the proximal connector end connected thereto to the pace/sense electrode, and means coupled to the transducer for determining capture of the heart by a delivered pacing pulse when a heart signal is provided by the transducer within a predetermined time period following delivery of the pacing pulse.

BRIEF DESCRIPTION OF THE DRAWINGS

Other objects, advantages and features of the present invention will be readily appreciated as the same becomes better understood by reference to the following detailed description when considered in connection with the accompanying drawings, in which like reference numerals designate like parts throughout the figures thereof and wherein:

FIG. 2 is a side cross-section view of a lead connector assembly taken along lines 2—2 of FIG. 1 within which at least a piezoelectric crystal pressure wave transducer and a reference transducer are incorporated in relation to the lead proximal connector end in accordance with a first embodiment of the invention;

FIG. 3 is an end cross-section view taken along lines 3—3 of the connector assembly of FIG. 2;

FIG. 4 is a side cross-section view of a lead connector assembly also taken along lines 2—2 of FIG. 1 within which at least a piezoelectric pressure wave transducer and a reference transducer are incorporated in relation to the lead proximal connector end in accordance with a second embodiment of the invention;

FIG. 5 is a side cross-section view of a lead connector assembly also taken along lines 2—2 of FIG. 1 within which an accelerometer pressure wave transducer is incorporated in in-line indirect mechanical contact the lead proximal connector end in accordance With a third embodiment of the invention;

FIG. 6 is a waveform diagram depicting the cardiac cycle pressure waves detected by a single pressure wave transducer in relation to preceding intrinsic PQRST complexes;

FIG. 7 is a waveform diagram depicting the respiration cycle pressure wave detected by a single pressure wave transducer in relation to a series of intrinsic PQRST complexes;

DETAILED DESCRIPTION OF THE PREFERRED EMBODIMENTS

The preferred embodiment of the invention is illustrated in the context of an implantable single or dual chamber pacemaker IPG of the type described in detail in the above-referenced '078, '643 and '406 patents or an implantable pacemaker-cardioverter-defibrillator IPG of the type described in commonly assigned U.S. Pat. No. 5,312,441, all incorporated herein by reference in their entireties. In such IPGs, the connector assembly is molded as a separate piece part and attached to the hermetically sealed case or can for the power source and electronic components in a manner shown, for example, in commonly assigned U.S. Pat. No. 5,070,605, incorporated herein by reference.

Figure 1:
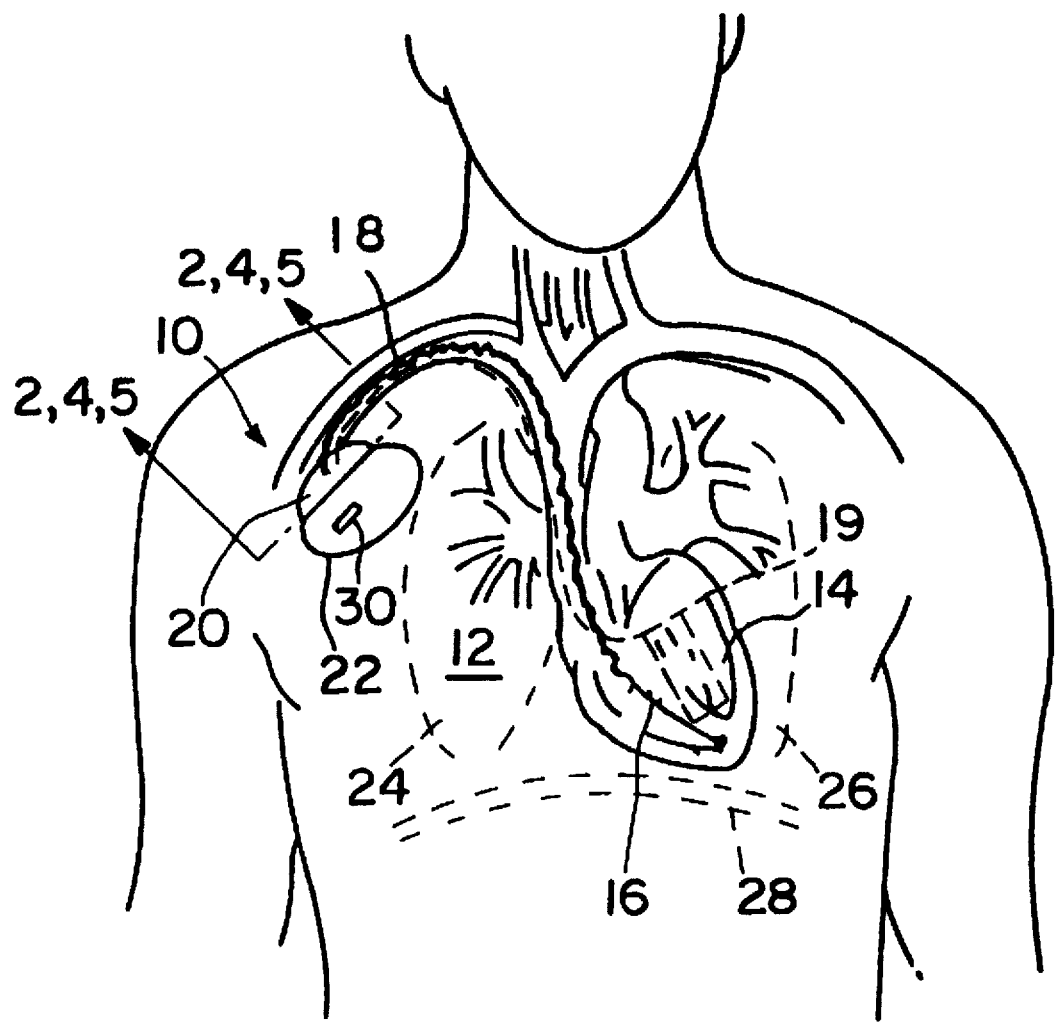
FIG. 1 is a schematic illustration of an IPG implanted in a patient's chest and an endocardial lead transvenously introduced into the heart and traversing the patient's chest.

FIG. 1 is a schematic illustration of such an IPG 10 implanted in a patient's chest 12 and an endocardial lead 18 (or leads) transvenously introduced into the heart 14 and traversing the patient's chest 12. The IPG 10 includes the connector assembly 20 and the case or can 22 enclosing the power supply and circuitry. The combination of the IPG 10 and the leads constitutes a pacemaker.

As the heart 14 contracts and expands, it creates cardiac contraction pressure waves which are transmitted into the distal end segment 16 of lead 18 and are conducted proximally to the relatively still IPG 10. The heart contraction may be intrinsic or it may be evoked by a pacing stimulus. Similarly, as the lungs 24, 26 expand and contract the pleural cavity and chest with the respiration cycle controlled by the diaphragm 28, the chest movement creates respiratory pressure waves that impart movement to the elongated lead 18 and are conducted proximally to the relatively still IPG 10.

Since the lead distal end segment 16 is typically firmly attached to the heart 14 (and may in fact be alternatively attached to the epicardium) so that good electrical contact is maintained, the cardiac contraction pressure wave may constitute a reaction to a physical shock, i.e. a rapid mechanical movement, imparted to the distal end segment of the relatively forceful contraction of the heart. The transmitted cardiac contraction pressure wave may comprise the mechanical movement itself effecting an acoustic or ringing response of the lead body and may include a component of the actual cardiac contraction sound, and we define it as such.

We have discovered that the cardiac contraction pressure wave, whatever its origin or constituents, may be readily detected at the proximal connector end of the lead 18 by a sensor in direct or indirect mechanical contact with the lead body. This discovery allows the replacement of sensors in the distal tip segment, which suffer the deficiencies detailed above, with a pressure wave sensor in the IPG (preferably in the connector block) in order to detect the evoked response of the heart to a preceding pacing pulse within an evoked response time window.

FIGS. 2 and 3 depict the lead connector module or assembly 20 coupled with a proximal connector end 40 of a lead 18 and the incorporation of a pressure wave transducer 32 and a reference transducer 34 in accordance with a first embodiment of the invention. Although a specific connector block and lead type are illustrated in the figures, it will be understood that the invention may be practiced with any lead configuration having in-line or bifurcated lead proximal connector ends and connector assembly configurations for such lead connector ends.

In this first embodiment, the transducers 32 and 34 are each formed of a piezoelectric crystal of the type employed as an activity sensor in commercially available MEDTRONIC® THERA® DR IPGs for rate-responsive pacing in the DDDR mode and other modes. In FIG. 1, such an activity sensor 30 is depicted adhered within the can 22. Such transducers 32, 34 are formed of a rectangular piezoelectric crystal of about 0.250×0.125×0.022 inches which is reduced in size from the activity sensor. The major opposed surfaces of the piezoelectric crystal 33 are coated with thin film electrodes 35 and 37, and the major opposed surfaces of the piezoelectric crystal 39 are coated with thin film electrodes 41 and 43 that are electrically attached to sensor lead wires as described below. The resulting capacitive transducer provides an electrical output signal on the lead sensor wires that varies in amplitude in response to minute deflections of the piezoelectric crystal in response to the cardiac contraction pressure waves.

It should be noted that the orientation of the reference transducer 34 should be in a parallel plane with plane of the pressure wave transducer 32, rather than in a transverse plane as depicted for convenience of illustration in the FIGS. 2 and 3. The parallel orientation provides a more exact response of both transducers to common made noise originating elsewhere in the body, for example.

It should also be noted that any transducer can be used, including for example those based on resonant microbeams, piezoresistive pressure sensitive diaphragms or whatever the reader prefers so long as they are of sufficient sensitivity and are responsive in the appropriate frequency range.

The connector assembly 20 shown in FIGS. 2 and 3 is similar to that described and shown in FIGS. 4–6 of the above-incorporated '605 patent. In particular, the connector 20 is formed of a connector housing 36 of uncolored, transparent epoxy molded to form an elongated, lead connector end bore 38 open at the tubular end 42 and terminating in a pin receptacle chamber 44. The connector housing 36 also encloses the transducers 32, 34, feedthrough terminal pins identified below and in-line lead retainers 50 and 52 described below. A flexible sleeve 48 fits over tubular end extension 46.

The bore 38 is shaped to receive the proximal connector end 40 of in-line, bipolar lead 18. The lead 18 is typically constructed of coaxially arranged and electrically insulated coiled wire conductors extending the length of an outer insulating sheath and forming the lead body surrounding a lumen 54 but may be constructed without a lumen. The proximal connector end 40 conforms to the IS-1 standard for bipolar in-line lead connectors and includes a proximal connector pin 56 coupled to the inner coiled wire conductor and sized to fit within the pin engaging, deflectable beam, lead retainer 50. An insulating sheath overlies the junction of the connector pin 56 and the inner coiled wire conductor and is formed with annular moisture sealing ribs 58 that engage the walls of the bore 38.

A connector ring 60 is coupled to the outer coiled wire conductor (not shown) and sized to fit within the pin engaging, deflectable beam, lead retainer 52. An insulating sheath overlies the junction of the connector ring 60 and the outer coiled wire conductor and is formed with further annular moisture sealing ribs 62 that engage the walls of the bore 38.

The lead connector end 40 is enlarged to a diameter 64 distally to the connector ring 60 and has an annular groove 66 in diameter 64 shaped to be retained in a necked down annular portion of the tubular end extension 46. The attachment of the lead connector end 40 in the bore 18 may be secured by a suture ring 68. The secure electrical connection of the connector pin 56 with the electrically conductive lead retainer 50 and the connector ring 60 with the electrically conductive lead retainer 52 is described in detail in the above-incorporated '605 patent.

A series of electrical feedthroughs 72, 74, 76, 78 are mounted to extend through the mating surface of the can 22 and into cavities 70 or 71 (preferably minimized into channels) sealed with medical grade silicone rubber adhesive or the like when the connector assembly 20 is attached to the can 22. Lead feedthrough pins 80 and 82 extend through the lead feedthroughs 74 and 78, respectively and are electrically connected to the lead retainers 50 and 52, respectively, by short wire conductors. Reference feedthrough pins 84 and 86 extend through double pin, reference feedthrough 72 and are electrically connected with the thin film electrodes 41 and 43, respectively, of the reference transducer 34 by short transducer wire conductors. Similarly, pressure wave feedthrough pins 88 and 90 extend through double pin, pressure wave feedthrough 76 and are electrically connected with the thin film electrodes 35 and 37, respectively, of pressure wave transducer 32 by short transducer wire conductors. Double pin transducer feedthroughs 72 and 76 may be employed because of the extremely low voltage and current signals generated by the pressure and reference wave transducers 32 and 34.

The connector assembly may be fabricated in one way by positioning the pressure and reference wave transducers 32, 34 and attached wires within opening 92 of cavity 70 and within cavity 71, respectively, and positioning the lead retainers 50 and 52 and attaching wires in the depicted enlarged open portions 96 and 98 of bore 38. The inserted components can then be fixed and sealed from the environment in those positions with silicone rubber adhesive while leaving the ends of the wires exposed for attachment to feedthrough pins. The backfilling of the gap between the pressure wave transducer 32 and the outer surface of the retainer 52 with silicone adhesive ensures that a direct mechanical contact is made with the lead retainer 52 and indirect contact is made with the lead body. Care must be taken to avoid entraining air bubbles in the backfilled silicone rubber adhesive insulating layer between the lead retainer 52 side wall and the adjacent conductive thin film electrode 35.

Alternatively as shown in FIG. 3, the pressure wave transducer 32 is carefully spaced from the lead retainer 52 by an electrical insulating layer 35 to prevent it from contacting the thin film electrode 35 while ensuring indirect contact through the lead retainer 52 to the lead body. In practice, the insulating layer 35 may be a more rigid plastic adhesive for adhering the lead retainer 52 and pressure wave transducer 32 (and associated sensor and retainer leads) together as a sub-assembly that is inserted into the open portion 98 before it is backfilled.

A further alternative approach providing direct contact of the lead retainer 52 with the piezoelectric crystal 33 can be practiced if the two electrodes are deposited on the side where electrode 37 is depicted. Intimate direct contact between the pressure wave transducer 32 and the lead retainer 52 can also be achieved by a thin layer of adhesive at the contact line.

In any case, the connector housing 36 may be formed with welding access ports through which a welding probe may be introduced to weld the conductor wire ends to the feedthrough pins as exemplified by welding ports 87 and 89 shown in FIG. 3. In this final assembly process, the connector assembly 20 is secured to the mating surface of can 22, and the conductor wire ends are welded to the feedthrough pins through the welding access ports. Then, the interior spaces 70, 71 (or channels) and the access ports are backfilled with medical grade silicone rubber adhesive.

The resulting connector assembly 20 of the first embodiment therefore includes a pressure wave transducer 32 that makes direct mechanical contact with the lead 18 and an reference transducer that is isolated from the lead 18 but subjected to common mode noise sources at the location of the IPG 10. For example, such common mode noise sources may include pressure waves induced by body or limb movement, speech, coughing, snoring, footfalls and extraneous ambient noise.

Turning to FIG. 4, it depicts an alternative arrangement of the locations of the piezoelectric crystal pressure wave transducer 32 and reference transducer 34. This orientation allows the direct conduction of mechanical pressure wave energy in the contraction pressure wave conveyed up the lead lumen 54 to deflect the piezoelectric crystal 33. The pressure wave transducer 32 is in direct axial alignment with the lead connector pin and mechanically coupled to it by a flexible spacer. e.g. a leaf spring 100. The leaf spring 100 is maintained in the end of the bore chamber 44 so that mechanical contact with the lead connector pin 56 may be maintained given lead and connector fit tolerances. As shown, the chamber 44 is extended to the thin film electrode 35 and the non-conductive leaf spring 100 fits in that space. A conductive leaf spring 100 may be used if the thin film electrode 35 is insulated or if the electrode 33 is located alongside electrode 35. All other aspects of the fabrication of the connector assembly 20 of FIG. 4 are similar to those described above.

The reference transducer 34 is located in a cavity 45 in molded housing 36 that is separated from the lead bore 38 by an internal wall of molded housing 36. Channels are also formed in the molded housing 36 to direct the transducer conductors to the reference feedthrough pins 84, 86. After the reference transducer 34 is positioned in the cavity 45, it is backfilled with silicone rubber adhesive.

In these embodiments of FIGS. 1–4, the placement of the reference transducer 34 and the related conductors and feedthrough 72 is arbitrarily depicted. They may be situated in the connector housing 36 at any convenient location that provides isolation from the pressure wave conducted up the lead 18. The preferred location and orientation of the reference transducer 34 and its related components is in a parallel plane to the plane of the pressure wave transducer 32. In an alternative embodiment, it is possible to eliminate the reference transducer 34 and associated components and employ the signals provided by the activity sensor 30 as reference signals for eliminating common mode noise.

The pressure wave transducer 32 may also be placed at any convenient angle to either of the lead retainers 50 and 52. Moreover, although a single channel IPG 10 is depicted for the sake of simplicity in the preceding drawings, it will be understood that the same approaches may be taken to provide a second pressure wave transducer in relation to a second lead for a dual chamber monitor or IPG of the types incorporated above and described below.

In addition, although piezoelectric crystal transducers of the type described are preferred due to their low cost, reliability, low current drain and responsiveness to pressure waves of the type described, piezoelectric crystal moving beam accelerometers may also be used. Other solid state, micro-miniaturized IC accelerometers and transducers may be substituted for the piezoelectric crystal transducers, including miniature IC beam accelerometers and capacitive accelerometers.

Turning now to FIG. 5, it depicts a further embodiment of the invention employing a micro-miniaturized, accelerometer 102 mounted in alignment with the lead connector pin 56 and in indirect contact therewith through a leaf spring 100. Such accelerometers are typically mounted on a diaphragm, and motion of the diaphragm effects motion of the moving element of the accelerometer.

The accelerometer 102 is inserted into the chamber 44 through an access port 47 in molded housing 36 that is backfilled with silicone rubber adhesive. The accelerometer leads 104, 106 are routed to pressure wave feedthrough pins 88, 90 of the pressure wave feedthrough 76. A reference accelerometer isolated from the pressure wave sensing accelerometer may also be provided in the embodiment of FIG. 5 in the same manner as the reference transducer 34 of FIGS. 2–4. All other aspects of the fabrication of the connector assembly 20 of FIG. 5 and its attachment to the can 22 are similar to those described above.

FIG. 6 is a two second waveform diagram depicting the cardiac cycle pressure wave in relation to the preceding intrinsic PQRST complex. The pressure wave is transmitted up a conventional pacing lead implanted in the ventricle of a healthy dog and detected by a pressure wave transducer in the connector block assembly 20. In this experiment, a wide bandpass filter was employed, and only the pressure wave transducer of the embodiment of FIGS. 2 and 3 was used. A lag between the peaks of the PQRST complex and the peaks of the double pulses is observed that is greater than the lag observed between the PQRST peaks and the peaks of the lub-dub sound waves observed using conventional chest electrodes and sound transducers as illustrated in the above-cited *RESEARCH DISCLOSURE* No. 37150. The double peaks of FIG. 6 may represent the pressure waveform of the ventricles in forcefully contracting and expelling blood and then relaxing and filling with blood that takes place in closer timed relation to the PQRST complex. A clear correlation between the double signal peaks of the pressure wave and the PQRST complex is observed. This correlation is effective with either an intrinsic depolarization or an evoked depolarization of the heart and in both the atrial and ventricular heart chambers.

FIG. 7 is a 20 second waveform diagram depicting the respiration cycle pressure wave detected by the pressure wave transducer in relation to a series of PQRST complexes in the same dog experiment. The respiration cycle is much longer than the cardiac cycle. Because the respiratory cycle alters the baseline amplitude of the pressure wave, the varying baseline signal may be derived and used to adjust the sensing threshold for the LOC detector.

Figure 8:
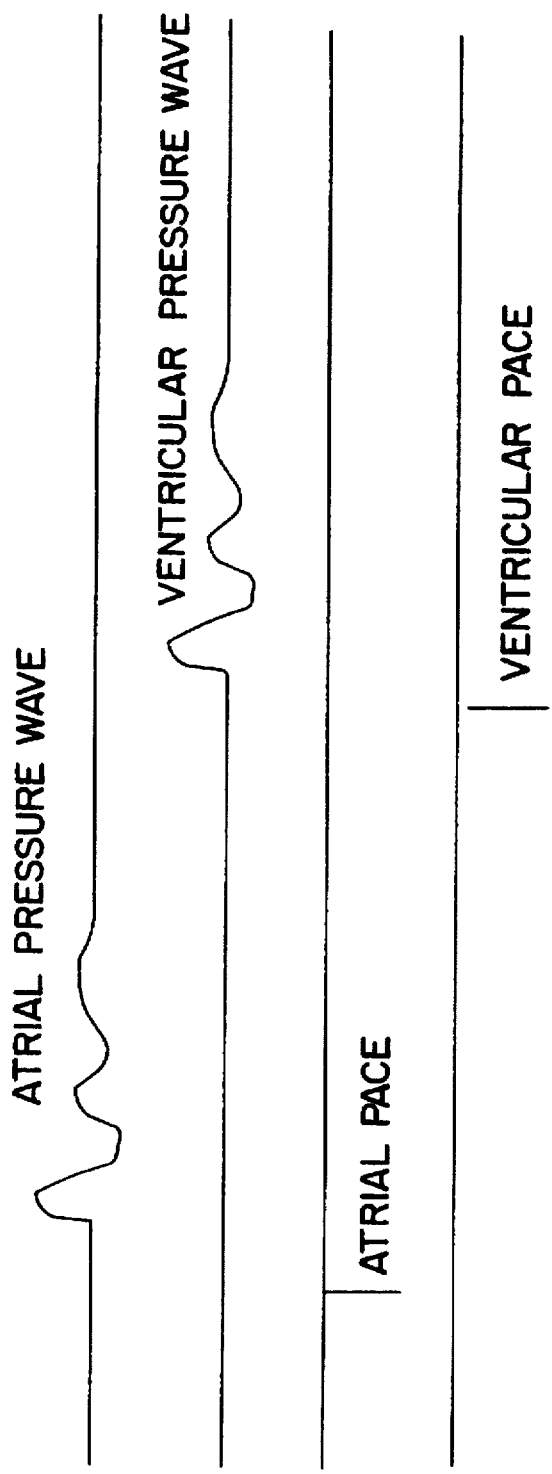
FIG. 8 is a waveform diagram depicting the cardiac cycle pressure waves detected by the atrial and ventricular pressure wave transducers in relation to preceding atrial and ventricular pacing pulses.

FIG. 8 is a waveform diagram depicting the cardiac cycle pressure waves detected by the atrial and ventricular pressure wave transducers in relation to preceding atrial and ventricular pace pulses. In each case, the pace pulse energy is sufficient to capture the atrium and the ventricle as indicated by the double pulse response of the atrial and ventricular pressure transducers located in the connector block assembly.

In this regard, at LOC, the double pressure pulse response is absent. Therefore, it is possible to determine LOC by comparing the signal amplitude to a pressure wave reference or threshold level that is derived as a function of the percentage of the average peak amplitudes of the depolarization related pressure waves and is adjusted to follow the amplitude of the respiratory pressure wave as described below.

Figure 9:
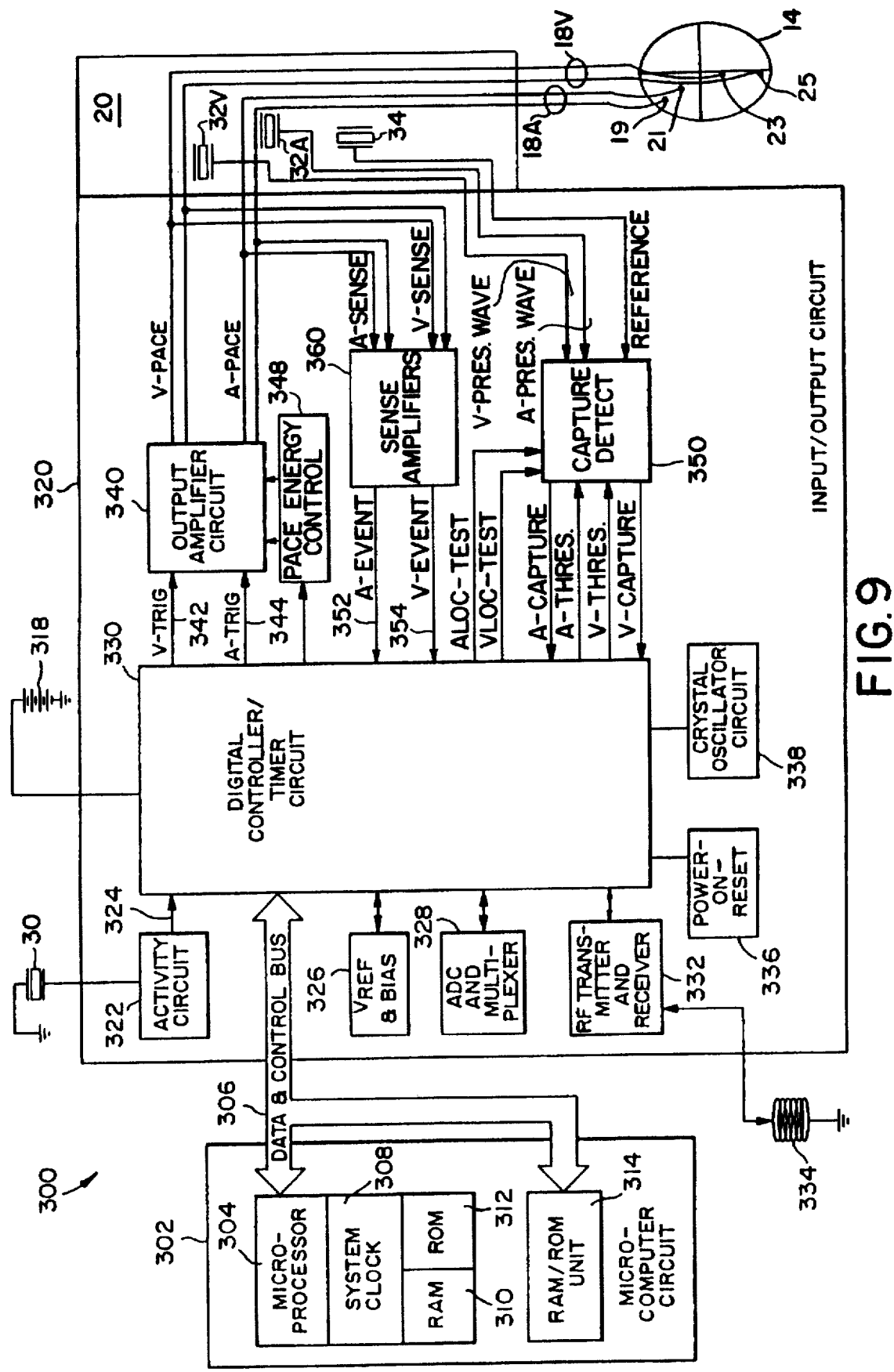
FIG. 9 is a block diagram of a dual chamber pacemaker in which the invention is preferably implemented for determining heart chamber capture/LOC at the pacing stimulation threshold in one or both heart chambers and for adjusting the atrial and/or ventricular pacing energy accordingly.

Turning now to FIG. 9, it depicts a block diagram of an IPG circuit 300 of an exemplary dual chamber, rate-responsive IPG 10 and set of atrial and ventricular pacing leads 18A and 18V in which the present invention may be practiced. The IPG 10 disclosed preferably operates in a DDD or DDDR pacing mode, wherein pacing pulses are delivered to both atrium and ventricle and wherein sensed atrial and ventricular depolarizations are both effective to inhibit delivery of the next scheduled pacing pulse in the chamber in which they are detected. The atrial and ventricular capture detection from the ventricular electrodes afforded by the present invention is believed optimally practiced in a pacemaker operating in the DDD, DDI, DVI, DDDR, DVIR and DDIR pacing modes.

It is readily apparent that this invention may be employed with single VVI pacemakers for capture detection using appropriately modified algorithms and circuits. It is not intended that this invention be only practiced with pacemakers that support DDR modes and one of ordinary skill can adapt these teachings based on the preferred implementation described here easily.

Lead 18A is an atrial bipolar pacing lead, carrying two electrodes 19 and 21 positioned in the right atrium of heart 14. Electrodes 19 and 21 are used both to sense and pace the atrium in a manner well known in the art. Similarly, lead 18V represents a ventricular bipolar pacing lead, carrying two electrodes 23 and 25 implanted in the right ventricle of the heart 14. As discussed above in conjunction with atrial lead 18A, electrodes 23 and 25 are used to sense and pace the ventricle in a manner well known in the art.

The IPG circuit 300 located within can 22 includes circuitry performing all of the basic timing, stimulation and sensing functions of a DDD or DDDR cardiac pacemaker. The IPG circuit 300 includes input/output circuit 320, a microcomputer circuit 302, which controls the timing intervals provided by the input/output circuit 320, a battery 318, an activity sensor 30 and a telemetry antenna 334 and the feedthroughs (not shown) to the connector block 20, as described above.

Crystal oscillator circuit 338 within input/output circuit 320 provides the basic timing clock for the components of the IPG circuit 300 through digital controller/timer circuit 330. Battery 318 provides power for all the components of IPG circuit 300. Power-on-reset circuit 336 within input/output circuit 320 responds to initial connection of the circuit to the battery 318 for defining an initial operating condition and also resets the operative state of the device in response to detection of a low battery voltage condition.

Reference mode circuit 326 within input/output circuit 320 generates stable voltage references and currents for the analog circuits within the pacing circuit 320. Analog to digital converter ADC and multiplexor circuit 328 within input/output circuit 320 digitizes analog signals and voltage to provide real time telemetry of cardiac signals from sense amplifiers 360 for uplink transmission via RF transmitter and receiver circuit 332. Voltage reference and bias circuit 326, ADC and multiplexor 328, power-on-reset circuit 336 and crystal oscillator circuit 338 may correspond to any of those presently used in current marketed implantable cardiac pacemakers.

In the embodiment illustrated in FIG. 9, the IPG 10 is provided with a piezoelectric crystal activity sensor 30 which is intended to monitor patient activity, in order to allow provision of DDDR rate responsive pacing, such that the defined pacing rate (A-A escape interval or V-V escape interval) increases with increased demand for oxygenated blood. Sensor 30 generates electrical pressure wave signals in response to sensed physical activity (patient footfalls) which are processed by activity circuit 322 in input/output circuit 320 to provide activity signal 324 to digital controller/timer circuit 330. Activity circuit 332 and associated activity sensor 30 may correspond to the circuit and sensor disclosed in U.S. Pat. Nos. 5,052,388 and 4,428,378, incorporated herein by reference in their entireties. Similarly, the present invention may be practiced in conjunction with alternate types of sensors such as oxygenation sensors, pressure sensors, pH sensors and respiration sensors, all well known for use in providing rate responsive pacing capabilities.

It should also be noted that in accordance with a further aspect of the present invention, the activity signal and respiration signal may be alternatively derived from signals processed from the sensors 32A, 32V and 34 as set forth in the above-referenced U.S. patent application Ser. No. 08/623,477. The present invention may also be practiced in non-rate-responsive pacemakers or while the DDDR pacemaker is operating in a non-rate-responsive mode.

Data transmission to and from the external programmer (not shown) is accomplished by means of the telemetry antenna 334 and an associated RF transmitter and receiver 322 within input/output circuit 320, which serves both to demodulate received downlink telemetry and to transmit uplink telemetry. For example, circuitry for demodulating and decoding downlink telemetry may correspond to that disclosed in U.S. Pat. No. 4,556,063, while uplink telemetry functions may be provided according to U.S. Pat. Nos. 5,127,404 and 4,374,382. Uplink telemetry capabilities will typically include the ability to transmit stored digital information as well as real time or stored EGMs of atrial and/or ventricular electrical activity (according to the teaching of the above-cited '404 patent), as well as transmission of Marker Channel pulses indicating the occurrence of sensed and paced depolarizations in the atrium and ventricle, as disclosed in the cited '382 patent.

In addition, in the context of the present invention, stimulation threshold data from a series of auto-capture test stimulation pace events may be stored in the RAM 310 or the RAM/ROM unit 314 of microcomputer 302 for later telemetry out on command of the external programmer. This data may be encoded in digital form and transmitted via RF transmitter 332 and antenna 334 to the external programmer 40 for display and/or analysis.

The connector block assembly 20 is also illustrated schematically in FIG. 9 in relation to the IPG circuit 300. The bipolar leads 18A and 18V are illustrated schematically coupled directly through the connector block assembly 20 and into the input/output circuit 320. The atrial and ventricular pressure wave sensors 32A and 32V, respectively, are shown schematically in proximity to the proximal connector ends of atrial and ventricular leads 18A and 18V. The reference transducer 34 is shown schematically within the connector block assembly 20. The associated terminals, lead wires and feedthroughs are not shown in FIG. 9. In the actual implantable device, connector block 20 and these components for both the atrial and ventricular leads would, of course, take one of the forms described in reference to FIGS. 1–5 and equivalents thereto.

A pace output amplifier circuit 340 in input/output circuit 320 includes a ventricular pulse generator circuit coupled to the ventricle of the heart 14 by means of electrodes 23, 25 on lead 18V as well as an atrial pulse generator circuit coupled to the atrium of heart 14 by means of atrial electrodes 19, 21, located on lead 18A. In order to trigger generation of a ventricular pacing or V-PACE pulse, digital controller/timer circuit 330 generates a trigger signal on V-TRIG line 342. Similarly, in order to trigger an atrial pacing or A-PACE pulse, digital controller/timer circuit 330 generates a trigger pulse on A-TRIG line 344. The A-PACE and V-PACE pulse energies may be controlled in either or both pulse width and pulse amplitude by pace energy control 348 which receives a pace energy command signal from digital timer/controller circuit 330 prior to the delivery of each A-TRIG and V-TRIG signal. In accordance with the present invention, the atrial and ventricular pace pulse energies are determined in response to the determination of the atrial and ventricular pacing thresholds as described below.

Sense amplifier circuit 360 includes atrial and ventricular sense amplifiers coupled to the atrium and ventricle by means of leads 18A and 18V, respectively. The output circuit 340 and sense amplifier circuit 360 may contain pulse generators and sense amplifiers corresponding to any of those presently employed in commercially marketed cardiac pacemakers. Sensed atrial depolarizations or P-waves that are confirmed by the atrial sense amplifier (A-EVENT) in response to an are communicated to the digital controller/timer circuit 330 on A-EVENT line 352. Similarly, ventricular depolarizations or R-waves that are confirmed by the ventricular sense amplifier (V-EVENT) in response to a V-SENSE are communicated to the digital controller/timer circuit 330 on V-EVENT line 354.

Control of timing and other functions within the input/output circuit 320 is provided by digital controller/timer circuit 330, which includes a set of timers and associated logic. Digital controller/timer circuit 330 defines the basic pacing or escape interval, which may take the form of an A-A escape interval initiated on atrial sensing (A-EVENT) or pacing (A-PACE) and triggering atrial pacing (A-PACE) at the expiration thereof or may take the form of a V-V escape interval, initiated on ventricular sensing (V-EVENT) or pacing (V-PACE) and triggering ventricular pulse pacing (V-PACE) at the expiration thereof. Digital controller/timer circuit 330 similarly defines the A-V delay intervals SAV and PAV that commence following a sensed A-EVENT and a delivered A-PACE, respectively. The specific values of the intervals defined are controlled by the microcomputer circuit 302 by means of data and control bus 306 from programmed in parameter values and operating modes.

Digital controller/timer circuit 330 also defines time intervals for controlling operation of the atrial and ventricular sense amplifiers in sense amplifier circuit 360. Typically, digital controller/timer circuit 330 defines an atrial blanking interval following delivery of an A-PACE pulse, during which atrial sensing is disabled, as well as ventricular blanking intervals following atrial and ventricular pacing pulse delivery, during which ventricular sensing is disabled. Digital controller/timer circuit 330 also defines an atrial refractory period (ARP) during which atrial sensing is disabled or the A-EVENT is ignored for the purpose of resetting the escape interval. The ARP extends from the beginning of the SAV or PAV interval following either an A-EVENT or an A-TRIG and until a predetermined time following sensing of a ventricular depolarization or triggering the delivery of a V-PACE pulse. Digital controller/timer circuit 330 similarly defines a ventricular refractory period (VRP), which is typically shorter than the portion of the ARP following ventricular sensing or pacing, following either a V-EVENT or V-TRIG.

In the case of an ectopic V-EVENT, both a VRP and a post-ventricular atrial refractory period (PVARP) defined by the digital controller/timer circuit 330 separately from the ARP may be generated. The durations of the ARP, PVARP and VRP may also be selected as a programmable parameter stored in the microcomputer 302. Digital controller/timer circuit 330 also controls sensitivity settings of the sense amplifiers 360 by means of sensitivity control 350.

Microcomputer 302 controls the operational functions of digital controller/timer circuit 330, specifying which timing intervals are employed, and controlling the duration of the various timing intervals, via data and control bus 306. Microcomputer 302 contains a microprocessor 304 and associated system clock 308 and on-processor RAM and ROM chips 310 and 312, respectively. In addition, microcomputer circuit 302 includes a separate RAM/ROM chip 314 to provide additional memory capacity. Microprocessor 304 is interrupt driven, operating in a reduced power consumption mode normally, and awakened in response to defined interrupt events, which may include the A-TRIG, V-TRIG, A-EVENT and V-EVENT signals.

In operation, if the IPG circuit 300 is programmed to a rate responsive mode, the patient's activity level is monitored periodically and the escape interval is adjusted proportionally. A timed interrupt, e.g., every two seconds, may be provided in order to allow the microprocessor 304 to analyze the output of the activity circuit 322 and update the basic escape interval (A-A or V-V) of the IPG. The microprocessor 304 may also define variable A-V intervals and variable ARPs and VRPs which vary with the escape interval established in response to patient activity. For example, the microprocessor 304 may specify a variable rate adaptive decrement interval (RAD) to be subtracted from the defined A-V delay intervals when the heart rate (paced or sensed) is above a defined resting or "start" rate. Similarly microprocessor 304 may define ARPs and/or VRPs which decrease in duration in relation to an increase in sensed or paced heart rate above the start rate.

The A-A interval is started, and during the A-V delay interval the device awaits either time out of the current A-V delay interval (PAV or SAV) or a V-EVENT. If a V-EVENT does not occur prior to A-V delay interval time out, a V-TRIG is generated at the end of the A-V interval, and the values of the A-V intervals are updated, if necessary. If a V-EVENT is sensed prior to expiration of the current A-V delay interval, the pacemaker's timing may be reset to deliver an A-TRIG at the expiration of a V-A escape interval or at the expiration of the A-A escape interval. If the A-A (or V-A) escape interval expires without any intervening A-EVENT or V-EVENT, an A-PACE pulse is again generated, and the next succeeding A-V delay interval is defined to be equal to a PAV. In the event that a V-EVENT is sensed at prior to expiration of the A-A escape interval, the timing is reset to trigger A-PACE at the expiration of the V-A interval (A-A escape interval minus PAV). If an A-EVENT is sensed prior to expiration of the A-A (or V-A) interval, the subsequent A-V interval is defined to be equal to SAV and the A-A escape and A-V delay intervals are reset. The time interval values, including the A-A escape interval, the SAV and PAV delay intervals, the ARP, VRP and any other time intervals defined by operating algorithms at any particular time are stored in either ROM or RAM and are fetched, used and updated as described above.

In the normal, everyday operation of the IPG, the A-PACE and V-PACE pulse energy in each case may be established initially by programming the pulse widths and amplitudes post-operatively or at a later patient examination. In accordance with the invention, the normal pacing operation is departed from on a periodic schedule or during a programmed-in threshold test operation to operate the capture detect circuit 350 in accordance with the algorithm of FIG. 13 for deriving both atrial and ventricular stimulation threshold data for storage in memory for telemetry out and analysis and also for use in setting the V-PACE and A-PACE normal pulse width and amplitude used between successive auto-capture tests in order to conserve battery energy. The pacemaker circuit 300 operating in accordance with this aspect of the present invention is capable of detecting atrial loss of capture (ALOC) and ventricular loss of capture (VLOC) in patients having a regular and predictable A-V conduction or first degree A-V block.

Figure 10:
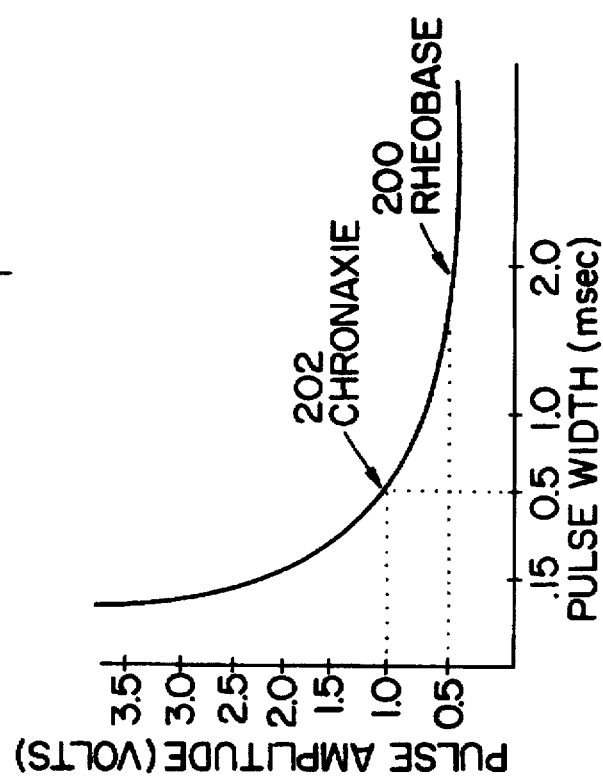
FIG. 10 shows a typical S-D curve for electrical stimulation of myocardial tissue plotted as pulse amplitude versus pulse width.

First the S-D characteristics taken into account in the operation of the invention are described in reference to FIG. 10 which shows a typical S-D curve for electrical stimulation of myocardial tissue plotted as pulse amplitude in volts versus pulse width in milliseconds corresponding generally to FIG. 2 of the above-referenced '643 patent. The graph shows, inter alia, that the stimulation threshold increases with a decreasing pulse width, and thus decreases with an increasing pulse width, except that beyond the Rheobase, no further reductions in the amplitude threshold can be achieved. Thus, increasing the pulse width beyond about one millisecond (in the example shown) still requires a threshold of 0.5 volts. Also included on the graph for illustrative purposes is the Chronaxie, a measure of myocardial excitability, which is the point representing the lowest pulse width needed to have an amplitude threshold equal to twice the Rheobase threshold.

It is well known in the art to provide a safety margin between the actual delivered pacing pulse width and amplitude and the stimulation thresholds appearing in the strength-duration curve. However, as previously stated, the amount of the safety margin may change over time and must be balanced against the need to maximize battery life, as increased amplitude and pulse width will cause a greater battery energy consumption. Physiological changes in the patient may alter the thresholds from the initial programmed value or values, and can lead to loss of capture, with inadequate amplitude or pulse width.

Returning to FIG. 9, the A-PRES., V-PRES., and REFERENCE wave signals developed by the atrial pressure wave sensor 32A, the ventricular pressure wave sensor 32V and the reference sensor 34 are applied to the capture detector 350. The capture detector is enabled by A-TEST and V-TEST time window signals to develop A-CAPTURE and V-CAPTURE signals as described below during the capture detection operation.

Figure 11:
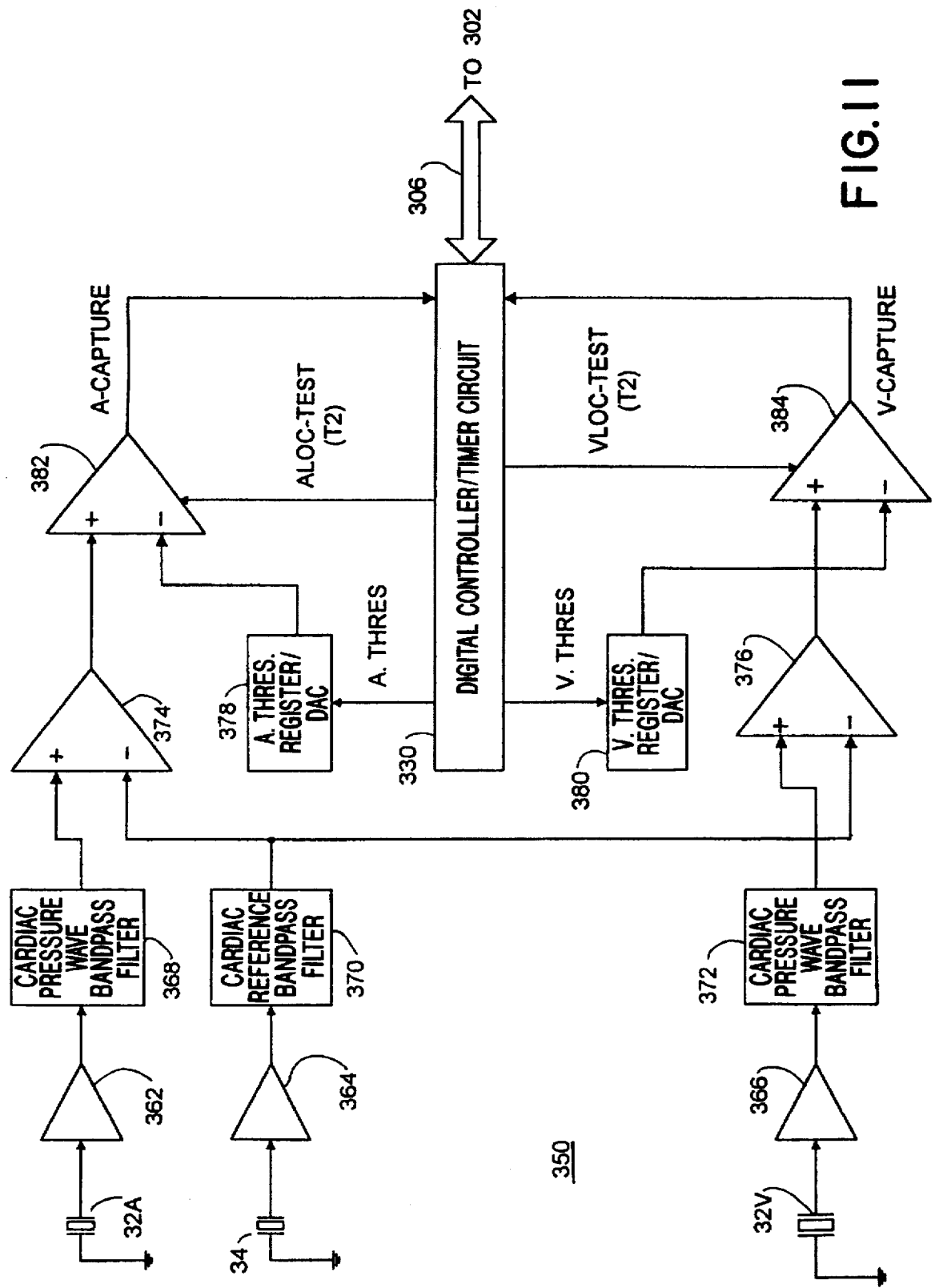
FIG. 11 is a block diagram of a signal processing system for processing the pressure wave and reference signals from the pressure wave and reference transducers.

Turning now to FIG. 11, it is a schematic block diagram of the capture detector 350 for processing the A-PRES, V-PRES and REFERENCE signals developed by each pressure wave transducer 32A, 32V and the reference transducer 34 (if present). The pressure wave and reference signals are first amplified in amplifiers 362, 364 and 366, respectively. The amplified pressure wave and reference signals are then bandpass filtered in bandpass filters 368, 370 and 372, respectively. Then, the amplified and filtered reference signal is subtracted from the amplified and filtered pressure wave signals in noise differential amplifiers 374 and 376.

The bandpass filter 368, 370, 372 characteristics are tailored to pass the range of amplified signal frequencies of interest and to reject frequency components in the signals that are outside that range. For example, the piezoelectric transducers as described above are sensitive to sound or motion frequencies of interest as well as to footfalls when the patient is ambulatory, muscle artifacts or myopotentials associated with limb movements and exercise, and may be responsive to speech and exterior environmental noise. These may constitute "noise" that are first filtered out to the extent possible and then subtracted in noise differential amplifiers 374 and 376 to derive the atrial or ventricular pressure wave signal of interest. The frequency range of the bandpass filters for each such channel is selected for the signal to be derived. In sensing amplitude and frequency components of the cardiac pressure wave, the frequency range of interest is believed to be between about 0.5–7.0 Hz in the atrium and in the ventricle but may be different depending on the waveform characteristic sought be detected.

In the context of the embodiment of FIG. 5 and in certain of the alternative uses of the invention described above, there may be no reference signal to employ, and the circuits of FIGS. 9 and 11 may accordingly be simplified. As stated above, the reference signal may also alternatively be provided by the activity sensor 30, if present.

The digital controller/timer circuit 330 provides the ALOC-TEST or the VLOC-TEST signals during the time period T2 described below with reference to FIG. 12 to enable atrial and ventricular threshold comparators 382 and 384, respectively. The filtered and amplified atrial and ventricular pressure wave signals of interest passed through noise differential amplifiers 374 and 376 are applied to one input of the atrial and ventricular threshold comparators 382 and 384, respectively. The A. THRES. or V. THRES. increment or decrement signal is applied by the digital controller/timer circuit 330 to the A. THRES. register/DAC 378 and the V. THRES. register/DAC 380, respectively. The A. THRES. and V. THRES. signals are converted to analog threshold signals and then applied to the other input terminals of the atrial and ventricular threshold comparators 382 and 384, respectively. In this manner, threshold analog signals are provided by digital controller/timer 330 and are applied to the other inputs of A-CAPTURE and V-CAPTURE threshold comparators 382 and 384. The A-CAPTURE and V-CAPTURE output signals of comparators 382 and 384 are developed when the respective filtered and amplified A-PRES. and V-PRES. signal peaks exceed the atrial and ventricular capture thresholds. The atrial and ventricular analog thresholds may be programmed values or derived as percentages of averaged peak values of the filtered and amplified A-PRES. and V-PRES. signals in a manner described in the processing of oxygen saturation threshold signals in the above-incorporated '406 patent.

The present invention provides a method of automatically determining atrial and ventricular pacing thresholds and ALOC and VLOC simply using the A-PRES. and V-PRES. evoked response signals. Thus, minimal additional hardware and software are necessary in the practice of the invention.

The stored values for both atrial and ventricular pulse width and pulse amplitude will be the actual measured values at CAPTURE or LOC or both as determined in the course of conducting the atrial and ventricular pacing threshold tests. The actual stimulation threshold data that are stored and later characterized as Rheobase and Chronaxie may therefore be selected as either the measured value declared as LOC or CAPTURE as described below.

It is intended that the SD algorithm operate automatically only during periods of sleep, and that, if possible, it be initiated about the same time every night by a programmed start time. The SD algorithm establishes a test pacing rate for the selected heart chamber that is clinically acceptable and not arrhythmogenic but is fast enough to prevent a patient from breaking through with a sinus escape mechanism which thereby causes inhibition of the pacemaker or leads to multiple fusion events. In this regard, the pacing rate during the test should not exceed 100 bpm to avoid intolerable patient symptoms from pacing rapidly in patients who may have coronary artery disease or may be sensitive to rapid stimulation. A rate of 60 to 100 bpm is fast enough to prevent intolerable symptoms when a beat is dropped due to LOC. Ventricular rate pauses during the recovery from VLOC described below should be no longer than two seconds.

Figure 12:
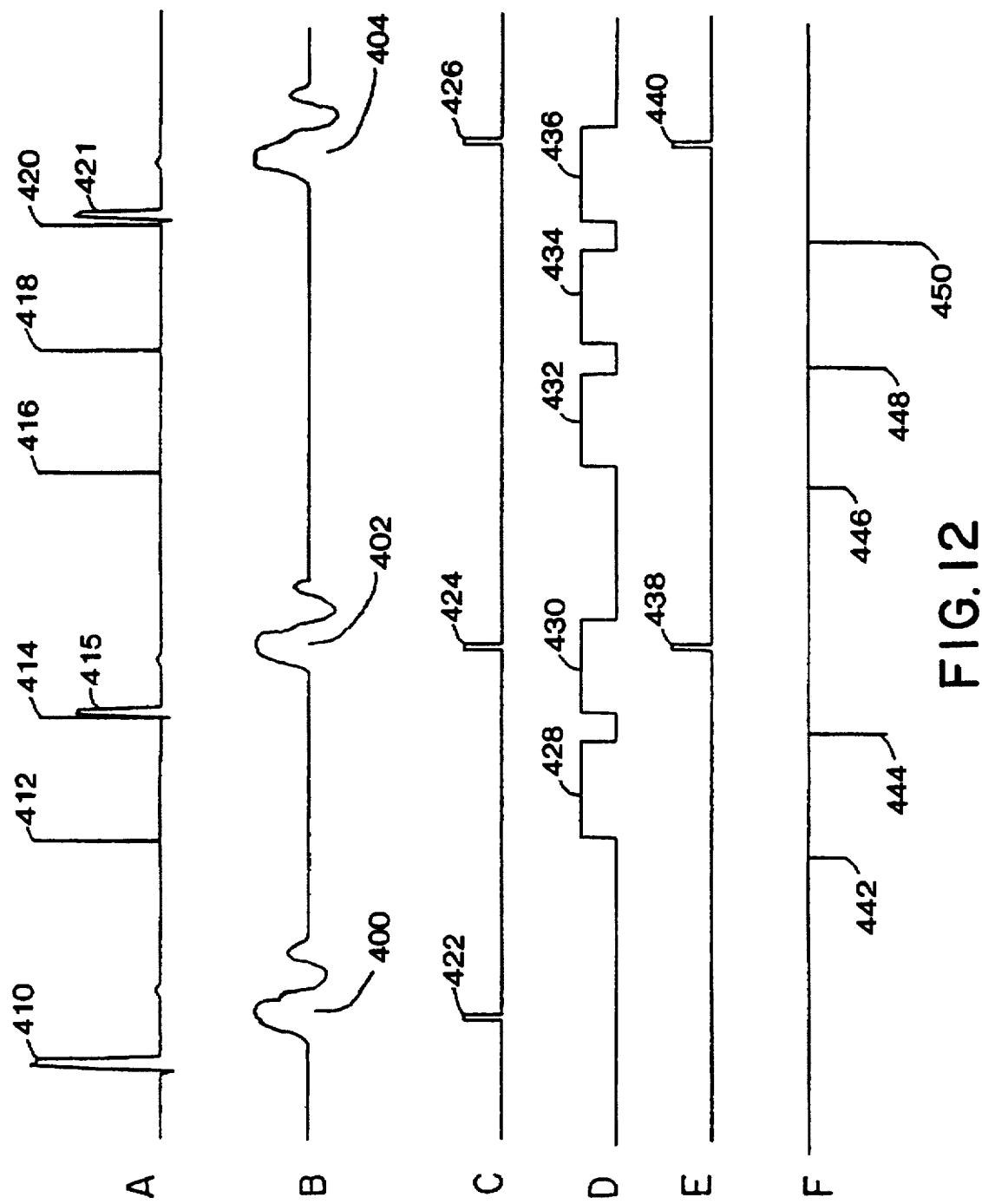
FIG. 12A–12F are timing diagrams which reflect the capture/LOC function timing window following a delivered pacing pulse by the pacemaker of FIG. 9.
Figure 13:
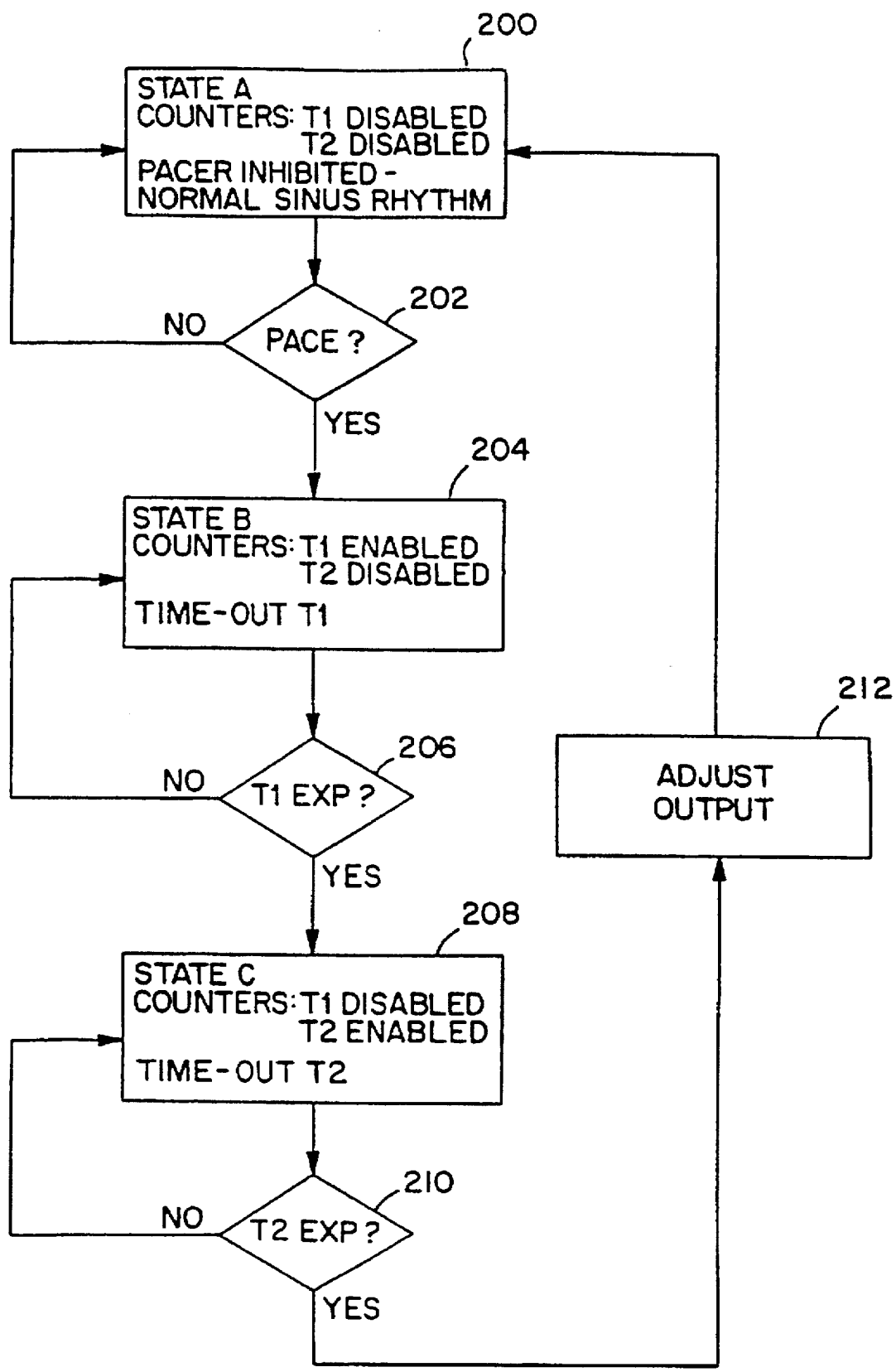
FIG. 13 is a machine description of a procedure for detecting the evoked response during the timing windows.

Turning to FIGS. 12 and 13, they depict a timing diagram which reflects the capture/LOC function timing window following a delivered pacing pulse by the pacemaker of FIG. 9 and a machine description of a procedure for detecting the evoked response during the timing windows for both the atrial and the ventricular channels.

The CAPTURE signal may be used in a variety of ways, and is illustrated herein in the context of an algorithm for testing for the pacing threshold or LOC threshold and for performing an auto-threshold adjustment of the pacing pulse energy to the detected threshold. In this instance, the CAPTURE/LOC detection test is initiated for each chamber by ALOC-TEST and VLOC-TEST signals provided to the capture detect circuit 350 from the digital controller/timer circuit 330. The current threshold level is also provided to the capture detect circuit 350 by the digital controller/timer circuit 330. The A-CAPTURE and V-CAPTURE signals are communicated to auto threshold logic in the digital controller/timer circuit 330. Auto threshold logic controls the energy content of the pacing pulses delivered by the output circuit 340 to the lead 18A or 18V.

In the event that a pacing pulse is delivered and no CAPTURE signal follows within a time window, the auto threshold logic generates a control signal to pace energy control circuit 348 to provide a backup pacing pulse at full energy and to increment the energy of the succeeding pacing pulses provided by output circuit 340.

Appropriate mechanisms for adjusting the energy content of the pacing pulses generated by output circuit 340 are disclosed in U.S. Pat. Nos. 4,858,610, 4,878,497, and 4,729,376, all of which are incorporated herein by reference in their entireties. Alternative pacing functions which may be modified in response to the detection or non-detection of cardiac depolarizations during the capture detect window are described in U.S. Pat. Nos. 4,795,366 and 4,305,396, both of which are incorporated herein by reference in their entireties.

The operation of the invention is illustrated in FIG. 12 which shows simulated Tracings of cardiac waveforms and associated pressure wave Tracing illustrating the theory underlying the present invention. Tracing A depicts the signals applied to and sensed by the sense amplifiers 360 on the pacing lead 18A or 18V. Tracing B depicts the V-PRES. or A-PRES. pressure wave signals occurring with respect to intrinsic or evoked cardiac depolarizations. Tracing C depicts the pressure wave detect signals processed from the pressure wave signal of Tracing B and the reference signal (if a reference transducer is employed) after comparison to a pressure wave threshold level in capture detect circuit 350 (FIG. 11). Tracing D depicts capture detect time windows of duration T2 that are triggered a short delay time T1 after the A-TRIG or V-TRIG signal and applied to the capture detection circuit 350. Tracing E depicts the A-CAPTURE or V-CAPTURE outputs of the capture detection circuit 348 and indicates the occurrence of an evoked response depolarization during the T2 time window.

Tracing F depicts markers corresponding to the A-PACE or V-PACE pulses of the output circuit 340 generated in response to the respective A-TRIG or V-TRIG signal and having an energy set by the pace energy control circuit 348 in response to the auto-threshold circuit. The amplitude of the pacing pulses are reflected by the height of the pulse markers. The occurrence of these pacing pulses is also reflected by the artifacts 412, 414, 416, 118 and 120 (Tracing A).

The first cardiac waveform 410 in Tracing A results from a normal sinus depolarization of the heart and is followed by a pressure wave 400. The pressure wave detect signal 422 on Tracing C reflects the normal detection of this event. However, since no timing window T2 is present on Tracing D, no CAPTURE signal is generated on Tracing E.

Artifact 412 on Tracing A and pacing pulse marker 442 on Tracing F indicate the delivery of a pacing pulse of reduced energy. A capture detect window 428 of duration T2 is defined thereafter as indicated on Tracing D. No cardiac depolarization and accompanying pressure wave results, as the pacing pulse is of insufficient amplitude to capture the heart. This LOC is logically determined in the auto-threshold circuit of digital controller/timer 330 from the absence of the CAPTURE signal. In this instance, the auto-threshold logic generates another pacing pulse at a programmed upper rate limit interval as indicated by artifact 414 in Tracing A. The amplitude of this pacing pulse is increased, as indicated by pacing pulse marker 444 in Tracing F.

In this instance, the second pacing pulse captures the heart as evidenced by the depolarization waveform 415 on Tracing A as well as the pressure wave 402 in Tracing B and the pressure wave detect signal 424 in Tracing C. This pressure wave detect signal 424 occurs within the capture detect window 430 following the delivery of pacing pulse at 414, as evidenced by V-SENSE detect signal 424 in Tracing C and capture detect signal 418 in Tracing E.

The Tracings associated with depolarization waveform 421 illustrates a sequence of three pacing pulse artifacts 416, 418, and 420. The first two pacing pulses of energy 446 and 448 fail to capture the heart, as indicated by the absence of CAPTURE signals in tracing E. Pacing pulse energy (pulse amplitude and/or width) is increased with each pace pulse, as indicated by pacing pulse markers 446, 448, and 450 (all at the programmable upper rate limit interval). The third pulse 420 is successful in capturing the heart as indicated by CAPTURE signal 440.

In FIG. 12, there is a delay of duration T 1 starting from the A-TRIG or V-TRIG signal depicted by pacing artifacts 412, 414, 416, 418 and 420 in Tracing A before the commencement of the capture detect windows of duration T2 depicted in Tracing D. The T1 duration should be short with an expected duration of about 10–50 milliseconds. The T2 duration should be long enough to allow a detection of any pacemaker triggered cardiac response. The inventors believe that about 100–300 milliseconds is an appropriate duration for T2. In practice, the T1 and T2 durations are preferably programmable.

FIG. 13 shows a hardware flow diagram setting forth a state machine description of the detection procedure performed by the circuitry of FIGS. 9 and 11 operating in the manner of FIG. 12. The flow chart of FIG. 13 and the timing diagram of FIG. 12 are applicable to either the atrial or ventricular channel, and so the following discussion will be with respect to the ventricular channel, for example.

In state A (200) shown in the flow diagram, both the T1 and T2 timing functions of a capture detection timer in digital controller/timer circuit 330 are disabled. This state corresponds to the pacer's operation during sinus rhythm which inhibits the pacemaker and when the capture detection and auto-threshold seeking functions are disabled. It will be assumed that the capture detection function is enabled either for periodic auto-threshold determination and associated pacing pulse energy setting or during a programmed-in capture detection mode.

State A is reentered upon the occurrence of each V-EVENT signal. The occurrence of a V-TRIG signal at decision block 202 forces a state transition to state B (204) where the T1 timing function is enabled. As the period T1 times out, the machine moves from state B (204) to state C (208) where the T2 window is being timed. A ventricular pressure wave detect signal occurring during the T2 window is accepted as the indication of an evoked response and a V-CAPTURE is declared in block 208. The expiration of the T2 time period without a V-CAPTURE being declared, tested at decision block 210, triggers adjustment of the pacing pulse amplitude at block 212, if necessary, and the return to state A (200).

The microcomputer 302 may be programmed with the algorithm to periodically, e.g. every night at a certain time when the patient would be sleeping, to automatically adjust the A-PACE and V-PACE output amplitude and pulse width to test for atrial and ventricular stimulation thresholds. The process followed derives and stores in RAM the Rheobase and Chronaxie stimulation threshold values resulting from the tests for later telemetry out and uses the values to automatically reset the normal pacing pulse width and amplitude, reflecting a safety margin, until the next test is conducted. In the process of testing for the thresholds, capture is restored on detection of ALOC and VLOC by applied backup A-PACE or V-PACE pulses at programmed pulse width and amplitude energy.

The automatically adjusted pace pulse parameter (amplitude or pulse width) may be referred to herein as the test stimulus "test value" or "metric", and the other parameter may be referred to herein as the test stimulus "fixed value" or "non-metric". The test value is adjusted throughout the stimulation threshold determination and recovery procedure described below (applicable to either ALOC or VLOC). The fixed value remains constant until the derivation of the LOC threshold values of the test value. The present invention may therefore follow the algorithms described, for example, in the above-incorporated '643 patent.

The illustrated IPG block diagram of FIG. 9 is merely exemplary, and corresponds to the general functional organization of most multi-programmable microprocessor controlled DDD(R) cardiac pacemakers presently commercially available. It is believed that the present invention is most readily practiced in the context of such an IPG, and that the present invention can therefore readily be practiced using the basic hardware of existing microprocessor controlled dual chamber pacemakers, as presently available, with the invention implemented primarily by means of modifications to the software stored in the ROM 312 of the microcomputer circuit 302. However, the present invention may also be usefully practiced by means of a full custom integrated circuit, for example, a circuit taking the form of a state machine in which a state counter serves to control an arithmetic logic unit to perform calculations according to a prescribed sequence of counter controlled steps. As such, the present invention should not be understood to be limited to a pacemaker having an architecture as illustrated in FIG. 9, and a circuit architecture as illustrated in FIG. 9 is not believed to be a prerequisite to enjoying the benefits of the present invention.

Finally, the sensing of the cardiac pressure waves in the manner described above may also be employed to confirm questionable sensing of P-waves and R-waves in the presence of electrical noise that can confuse the atrial and ventricular sense amplifiers.

While there has been shown what are considered to be the preferred embodiments of the invention, it will be manifest that many changes and modifications may be made therein without departing from the essential spirit of the invention. It is intended, therefore, in the following claims to cover all such changes and modifications as may fall within the true scope of the invention.

PARTS LIST FOR FIGS. 1–13

IPG 10
patient's chest 12
heart 14
distal end segment 16
endocardial lead 18
atrial lead 18A
ventricular lead 18V
atrial electrodes 19, 21
connector assembly 20
case or can
ventricular electrodes 23, 25
lungs 24, 26
diaphragm 28
activity sensor 30
pressure wave transducer 32
atrial pressure wave transducer 32A
ventricular pressure wave transducer 32V
piezoelectric crystal 33, 39
reference transducer 34
thin film electrode 35, 37, 41, 43
connector housing 36
lead connector end bore 38
proximal connector end 40
tubular end 42
pin receptacle chamber 44
cavity 45
tubular end extension 46
access port 47
flexible sleeve 48
in-line lead retainers 50, 52
lumen 54
proximal connector pin 56
annular moisture sealing ribs 58 connector ring 60
annular moisture sealing ribs 62
diameter 64
insulating layer 65
annular groove 66
suture ring 68
cavities 70, 71
double pin reference feedthrough 72
lead feedthrough 74, 78
double pin pressure wave feedthrough 76
lead feedthrough pin 80, 82
reference feedthrough pin 84, 86
welding ports 87 and 89
pressure wave feedthrough pin 88, 90
opening 92
enlarged section 96, 98
leaf spring 100
accelerometer 102
accelerometer leads 104, 106
amplifier 110, 112
bandpass filter 114, 116
comparator 118
signal processor 120
operating system 122
sense amplifier 124
blocks 200, 202, 204, 206, 208, 210, 212
IPG circuit 300
microcomputer circuit 302
microprocessor 304
data and control bus 306
system clock 308
on-processor RAM chip 310
on-processor ROM chip 312
RAM/ROM unit 314
battery 318
input/output circuit 320
activity circuit 322
activity signal 324
reference mode circuit 326
ADC and multiplexor circuit 328
digital controller/timer circuit 330
RF transmitter and receiver circuit 332
telemetry antenna 334
power-on-reset circuit 336
crystal oscillator circuit 338
pace output amplifier circuit 340
V-TRIG line 342
A-TRIG line 344
pace energy control 348
capture detect circuit 350
A-EVENT line 352
V-EVENT line 354
sense amplifier circuit 360
amplifiers 362, 364, 366
bandpass filters 368, 370, 372
noise comparators 374, 376
peak detectors 378, 380
threshold comparators 382, 384

We claim:

1. In a cardiac pacemaker, a system for verifying capture of the heart following delivery of a pacing pulse comprising:
   a pacing lead comprising:
     an elongated lead body extending between a proximal connector end and a distal end adapted to be placed in association with the heart such that a pressure wave in the heart caused by the depolarization of the heart is transmitted through said lead body to said proximal connector end;
     a pace/sense electrode at the distal end of said lead body; and
     a pacing lead conductor extending between said proximal connector end and said pace/sense electrode for conducting pacing pulses from said proximal connector end to said pace/sense electrode; and
   a cardiac pacemaker pulse generator comprising:
     a connector assembly for attachment with said proximal connector end, said connector assembly having a pressure wave detection transducer mounted therein in relation to said proximal connector end for detecting said pressure wave and providing a heart pressure wave signal representative thereof;
     pulse generator means for generating and delivering a pacing pulse through said connector assembly and said proximal connector end connected thereto to said pacing electrode;
     means for timing a capture detection time window following generation of a pacing pulse; and
     means coupled to said pressure wave detection transducer for determining capture of the heart by a delivered pacing pulse in response to a heart pressure signal provided by said pressure wave detection transducer within said capture detection time window.

2. The system of claim 1 further comprising:
   a reference transducer mounted in said pulse generator and isolated from said proximal connector end for detecting common mode noise signals and providing a reference signal in response thereto; and
   means for processing said reference signal and said pressure wave signal for removing common mode noise and detecting pressure waves associated with depolarization of the heart.

3. The system of claim 2 wherein said pressure wave detection transducer is affixed within said connector assembly so as to be adapted and disposed to ensure direct physical contact with said proximal connector end, for the transfer of said pressure waves through said direct physical contact.

4. The system of claim 3 wherein said pressure wave detection transducer and said reference transducer comprise piezoelectric crystal transducers.

5. The system of claim 1 wherein said pressure wave detection transducer is affixed within said connector assembly so as to be adapted and disposed to ensure direct physical contact with said proximal connector end, for the transfer of said pressure waves through said direct physical contact.

6. The system of claim 5 wherein said pressure wave detection transducer comprises a piezoelectric crystal transducer adapted to be deflected by pressure waves traveling through said lead body to said proximal connector end and by physical vibration of said proximal connector end in response thereto.

7. The system of claim 6 wherein:
   said connector assembly includes a connector bore for receiving and attaching with said proximal connector end; and
   said piezoelectric crystal transducer is mounted in axial alignment with said connector bore for axial alignment with said proximal connector end inserted into said bore.

8. The system of claim 6 wherein:
   said connector assembly includes a connector bore for receiving and attaching with said proximal connector end; and
   said piezoelectric crystal transducer is mounted alongside said connector bore for physical contact with said proximal connector end inserted into said connector bore.

9. The system of claim 1 wherein:

said connector assembly includes a connector bore for receiving and attaching with said proximal connector end; and said pressure wave transducer is mounted in axial alignment with said connector bore for axial alignment with said proximal connector end inserted into said bore.

10. The system of claim 1 wherein:

said connector assembly includes a connector bore for receiving and attaching with said proximal connector end; and said pressure wave transducer is mounted alongside said connector bore for physical contact with said proximal connector end inserted into said connector bore.

11. The system of claim 1 wherein:

said signal processing means further comprises means for bandpass filtering said pressure wave signals to detect signals associated with the contraction of the heart.

12. The system of claim 11 further comprising:

a reference transducer mounted in said connector assembly and isolated from said proximal connector end for detecting common mode noise signals and providing a reference signal in response thereto; and wherein said signal processing means further comprises:

means responsive to said reference signal and said pressure wave signal for removing common mode noise and detecting pressure waves associated with the contraction of the heart.

13. An apparatus adapted to be implanted within a patient for detecting an evoked response of cardiac tissue evoked by a pacing pulse, comprising:

a pulse generator for generating pacing pulses;

lead means for applying said pacing pulses to the heart having a proximal connector end;

sensing means positioned in proximity with said proximal connector end for sensing pressure waves from depolarization of the heart in response to an evoked depolarization thereof caused by a pacing pulse transmitted through said lead body directly to said proximal connector end, said sensing means generating a pressure wave signal representative thereof;

monitoring circuit means coupled to said sensing means for monitoring said pressure wave signal provided from said sensing means in response to the occurrence of a cardiac evoked response;

a capture detect timer defining a capture detect window after the generation of a pacing pulse by said pulse generator; and capture detect logic means responsive to said monitoring circuit means and said capture detect timer for detecting the occurrence of said evoked response occurring within said capture detect window.

14. The apparatus of claim 13 further comprising lead connector means for connecting said proximal connector end to said pulse generator and wherein said sensing means is positioned in said lead connector means in proximity with said lead connector end.

15. The apparatus of claim 14 further comprising:

a reference transducer mounted in said lead connector means and isolated from said proximal connector end for detecting common mode noise signals and providing a reference signal in response thereto; and means for processing said reference signal and said pressure wave signal for removing common mode noise and detecting pressure waves associated with depolarization of the heart.

16. The apparatus of claim 13 wherein said capture detect timer comprises:

a first timer defining a first time interval following the generation of said pacing pulse; and a second timer defining a capture detect time window beginning with the expiration of said first time interval.

17. The apparatus of claim 15 further comprising auto threshold logic coupled to said pulse generator and responsive to said capture detect logic means for altering the energy content of said pacing pulses in response to the occurrence or non-occurrence of a detected cardiac evoked response within said capture detect window.

18. The apparatus of claim 17 wherein said auto threshold logic comprises means for incrementing the energy content of said pacing pulses in response to the non-occurrence of a cardiac evoked response within the capture detect window.

\* \* \* \* \*